US009885352B2

(12) United States Patent
Yuan

(10) Patent No.: US 9,885,352 B2
(45) Date of Patent: Feb. 6, 2018

(54) SELECTABLE VALVE OF A DELIVERY SYSTEM

(71) Applicant: Genia Technologies, Inc., Mountain View, CA (US)

(72) Inventor: Robert A. Yuan, San Jose, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 148 days.

(21) Appl. No.: 14/867,918

(22) Filed: Sep. 28, 2015

(65) Prior Publication Data

US 2016/0146365 A1 May 26, 2016

Related U.S. Application Data

(60) Provisional application No. 62/084,379, filed on Nov. 25, 2014.

(51) Int. Cl.
| | |
|---|---|
| *B01L 3/00* | (2006.01) |
| *G01N 1/10* | (2006.01) |
| *B01L 99/00* | (2010.01) |
| *F16K 3/00* | (2006.01) |
| *F04B 53/10* | (2006.01) |
| *F16K 27/00* | (2006.01) |
| *G01N 33/487* | (2006.01) |

(52) U.S. Cl.
CPC ........ *F04B 53/10* (2013.01); *B01L 3/502715* (2013.01); *B01L 3/502738* (2013.01); *F16K 27/003* (2013.01); *B01L 2200/027* (2013.01); *B01L 2200/0663* (2013.01); *B01L 2300/0627* (2013.01); *B01L 2300/0867* (2013.01); *B01L 2400/0644* (2013.01); *G01N 33/48721* (2013.01)

(58) Field of Classification Search
CPC ... B01L 99/00; B01L 3/00; F16K 3/00; G01N 1/10
USPC ....... 422/502, 503, 504, 537, 538, 539, 540, 422/114, 541, 542, 543, 544, 417; 436/43, 180; 137/599.01, 602, 892, 605, 137/861, 613, 616.7
See application file for complete search history.

(56) References Cited

U.S. PATENT DOCUMENTS

| | | | |
|---|---|---|---|
| 5,695,720 | A | 12/1997 | Wade et al. |
| 6,813,568 | B2 | 11/2004 | Powell et al. |
| 7,481,787 | B2 | 1/2009 | Gable et al. |
| 8,110,148 | B2 | 2/2012 | Ball et al. |

(Continued)

FOREIGN PATENT DOCUMENTS

| | | |
|---|---|---|
| WO | 2010138186 | 12/2010 |
| WO | 2012042226 | 4/2012 |

*Primary Examiner* — Brian J Sines
(74) *Attorney, Agent, or Firm* — Van Pelt, Yi & James LLP

(57) ABSTRACT

A delivery system for a sensor chip includes a plurality of selectable ports arranged on a first assembly. Each of the selectable ports is in communication with a separate channel. The delivery system includes a second assembly movable in relation to the first assembly. The second assembly has a channel that is mechanically connectable to different ones of the plurality of selectable ports on the first assembly by motion of the second assembly relative to the first assembly. The delivery system includes a mechanical interface configured to engage a separate actuator so that relative motion of the first assembly and the second assembly is affected by the actuator.

25 Claims, 15 Drawing Sheets

(56) References Cited

U.S. PATENT DOCUMENTS

| | | |
|---|---|---|
| 8,263,336 B2 | 9/2012 | Rothberg et al. |
| 8,546,128 B2 | 10/2013 | Schultz et al. |
| 8,574,835 B2 | 11/2013 | Hinz et al. |
| 8,592,153 B1 | 11/2013 | Bustillo et al. |
| 8,592,154 B2 | 11/2013 | Rearick |
| 8,623,789 B2 | 1/2014 | Belgrader et al. |
| 8,673,627 B2 | 3/2014 | Nobile et al. |
| 8,698,212 B2 | 4/2014 | Milgrew |
| 8,742,469 B2 | 6/2014 | Milgrew |
| 8,748,947 B2 | 6/2014 | Milgrew |
| 8,766,327 B2 | 7/2014 | Milgrew |
| 8,776,573 B2 | 7/2014 | Rearick et al. |
| 8,822,205 B2 | 9/2014 | Milgrew |
| 8,846,378 B2 | 9/2014 | Schultz et al. |
| 2004/0028566 A1 | 2/2004 | Ko |
| 2007/0037199 A1 | 2/2007 | Takahashi |
| 2007/0068573 A1 | 3/2007 | Cox et al. |
| 2007/0166199 A1 | 7/2007 | Zhou et al. |
| 2008/0273918 A1 | 11/2008 | Linder |
| 2009/0026082 A1 | 1/2009 | Rothberg et al. |
| 2010/0113762 A1* | 5/2010 | Ball .................... B01J 19/0093 536/28.53 |
| 2010/0137143 A1 | 6/2010 | Rothberg et al. |
| 2010/0252116 A1 | 10/2010 | Kilcoin et al. |
| 2010/0285522 A1 | 11/2010 | Su et al. |
| 2010/0300559 A1* | 12/2010 | Schultz .............. B01L 3/502738 137/561 A |
| 2010/0301398 A1 | 12/2010 | Rothberg et al. |
| 2010/0322604 A1 | 12/2010 | Fondurulia |
| 2011/0094600 A1* | 4/2011 | Bergeron .......... B01L 3/502738 137/38 |
| 2011/0127455 A1* | 6/2011 | Hunnicutt ............ B81B 3/0051 251/284 |
| 2011/0207621 A1 | 8/2011 | Montagu et al. |
| 2012/0073667 A1 | 3/2012 | Schultz et al. |
| 2012/0074165 A1 | 3/2012 | Schultz et al. |
| 2012/0149603 A1* | 6/2012 | Cooney ................ B01L 3/5025 506/39 |
| 2014/0163521 A1 | 6/2014 | O'Connor |
| 2014/0194305 A1 | 7/2014 | Kayyem et al. |
| 2015/0190810 A1* | 7/2015 | Glezer .............. B01L 3/502738 436/180 |
| 2015/0308578 A1* | 10/2015 | Block, III ........... F04B 43/1269 137/1 |

* cited by examiner

SELECTABLE VALVE OF A DELIVERY SYSTEM

CROSS REFERENCE TO OTHER APPLICATIONS

This application claims priority to U.S. Provisional Patent Application No. 62/084,379 entitled RADIAL VALVE filed Nov. 25, 2014 which is incorporated herein by reference for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. Often utilizing a biochip requires liquid, gas, or other substances to be deposited and removed in a controlled sequence on or near the biochip. For example, various reagents and biological samples are flowed over the biochip in a controlled sequence to prepare the biochip, perform a measurement using the biochip, and clean the biochip for a next measurement. Manually performing this sequence is slow, error prone, and cost ineffective. Additionally, the transitioning from one measurement sample to a next measurement sample has been typically inefficient due to the steps involved in cleaning, resetting, refilling, and replacing various components. It would be desirable to develop items and techniques that are more efficient, robust, and cost-effective.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore-based sequencing chip may be used for DNA sequencing. A nanopore-based sequencing chip incorporates a large number of sensor cells configured as an array. For example, an array of one million cells may include 1000 rows by 1000 columns of cells.

Figure 1:
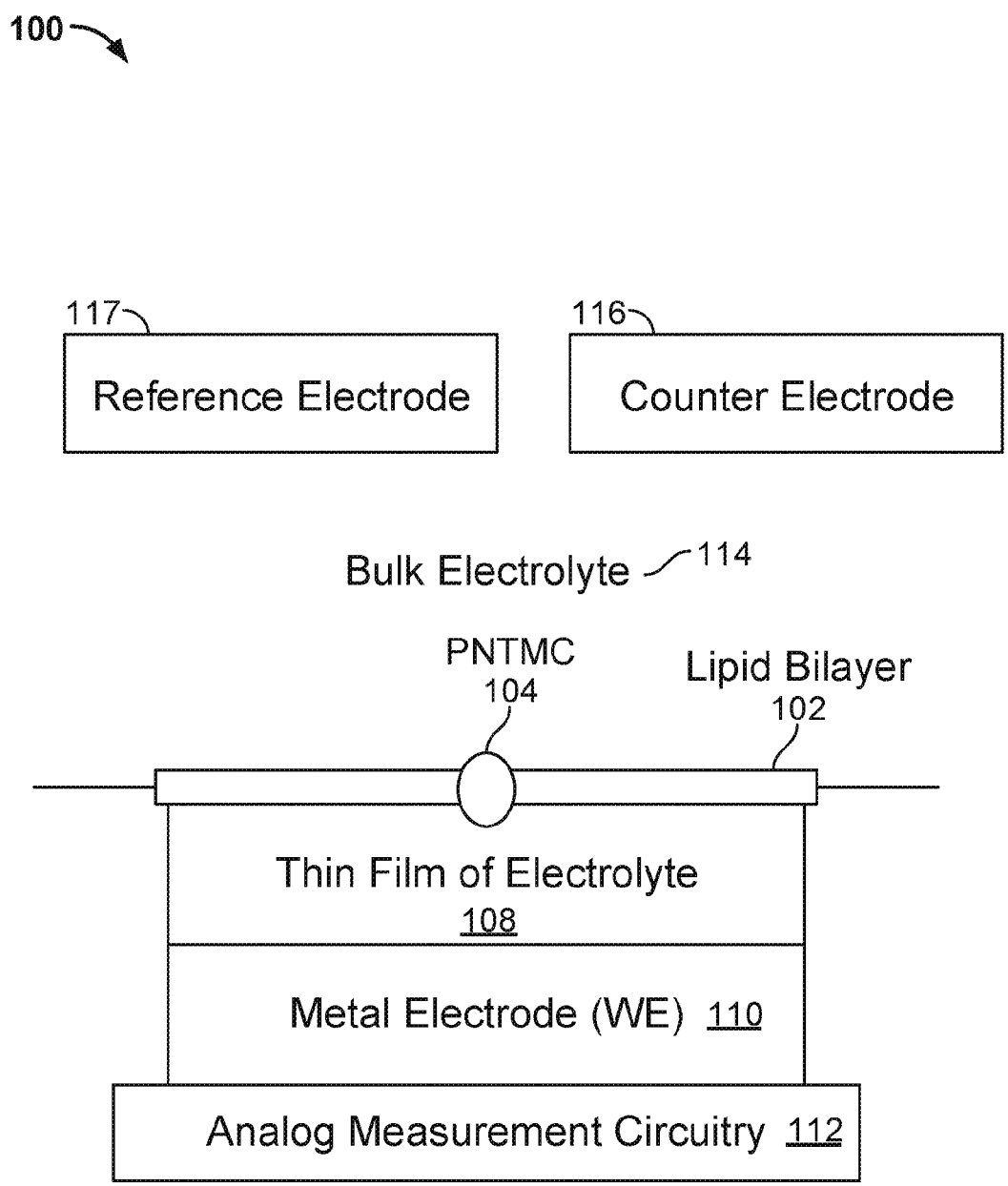
FIG. 1 illustrates an embodiment of a cell 100 in a nanopore-based sequencing chip.

FIG. 1 illustrates an embodiment of a cell 100 in a nanopore-based sequencing chip. A membrane 102 is formed over the surface of the cell. In some embodiments, membrane 102 is a lipid bilayer. The bulk electrolyte 114 containing protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor. The cell also includes a reference electrode 117.

Figure 2:
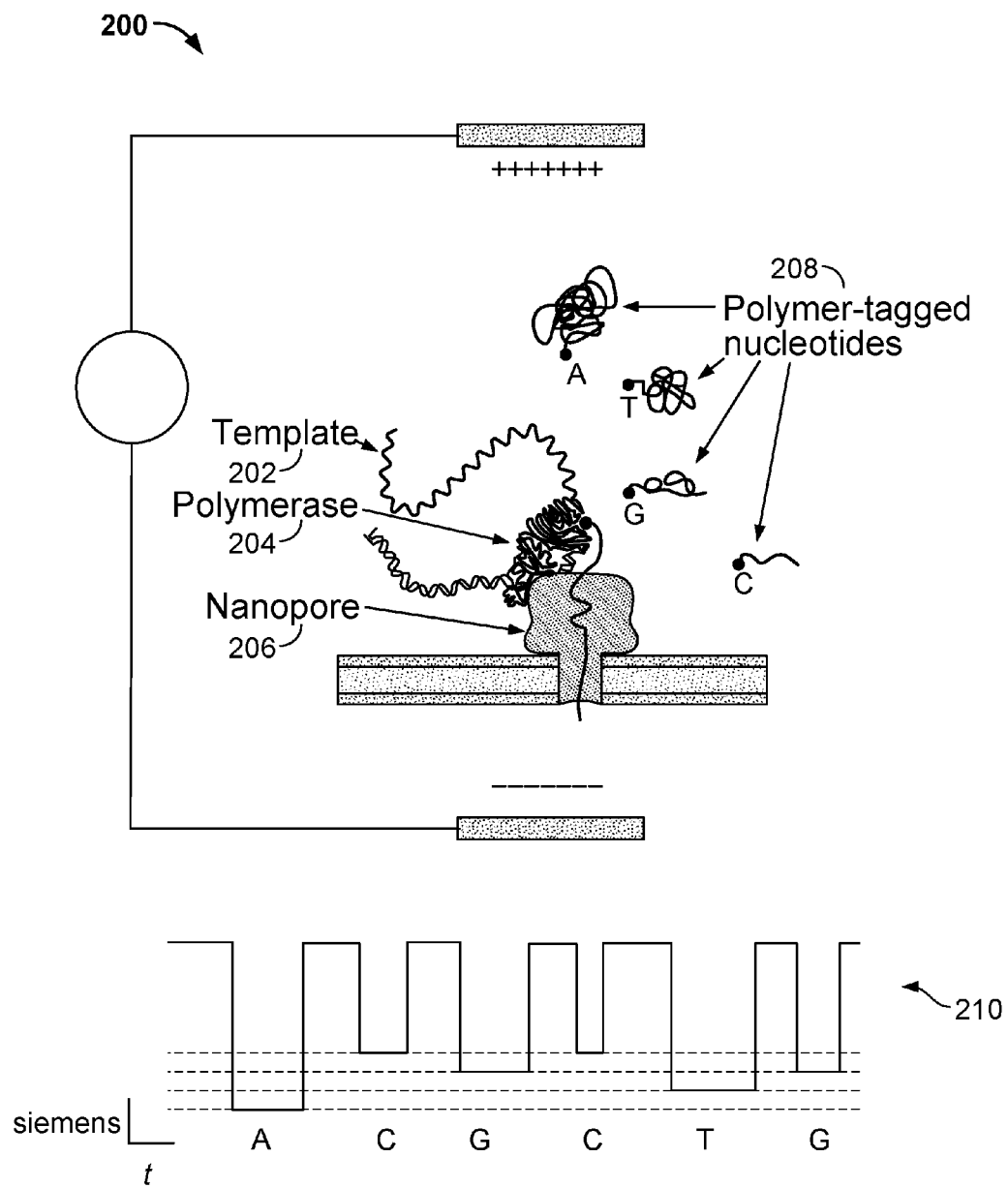
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
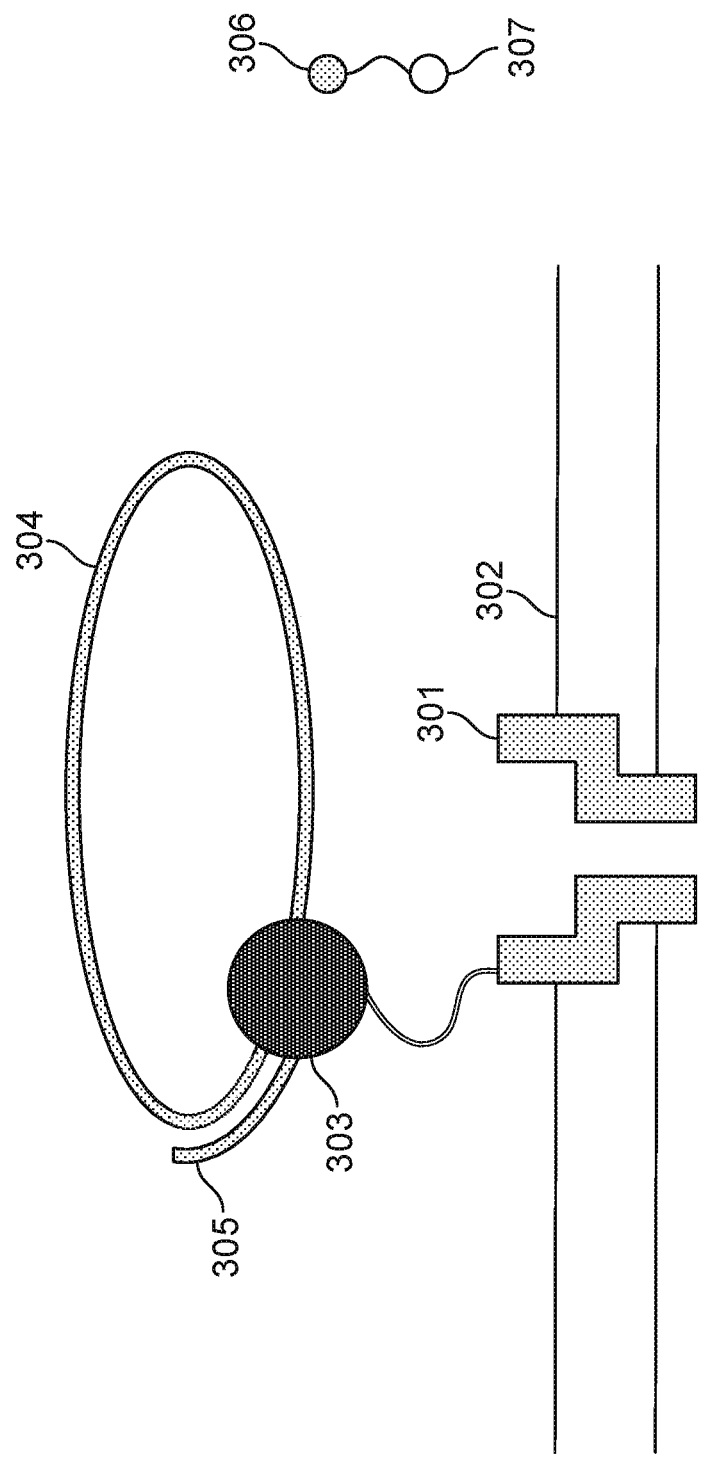
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
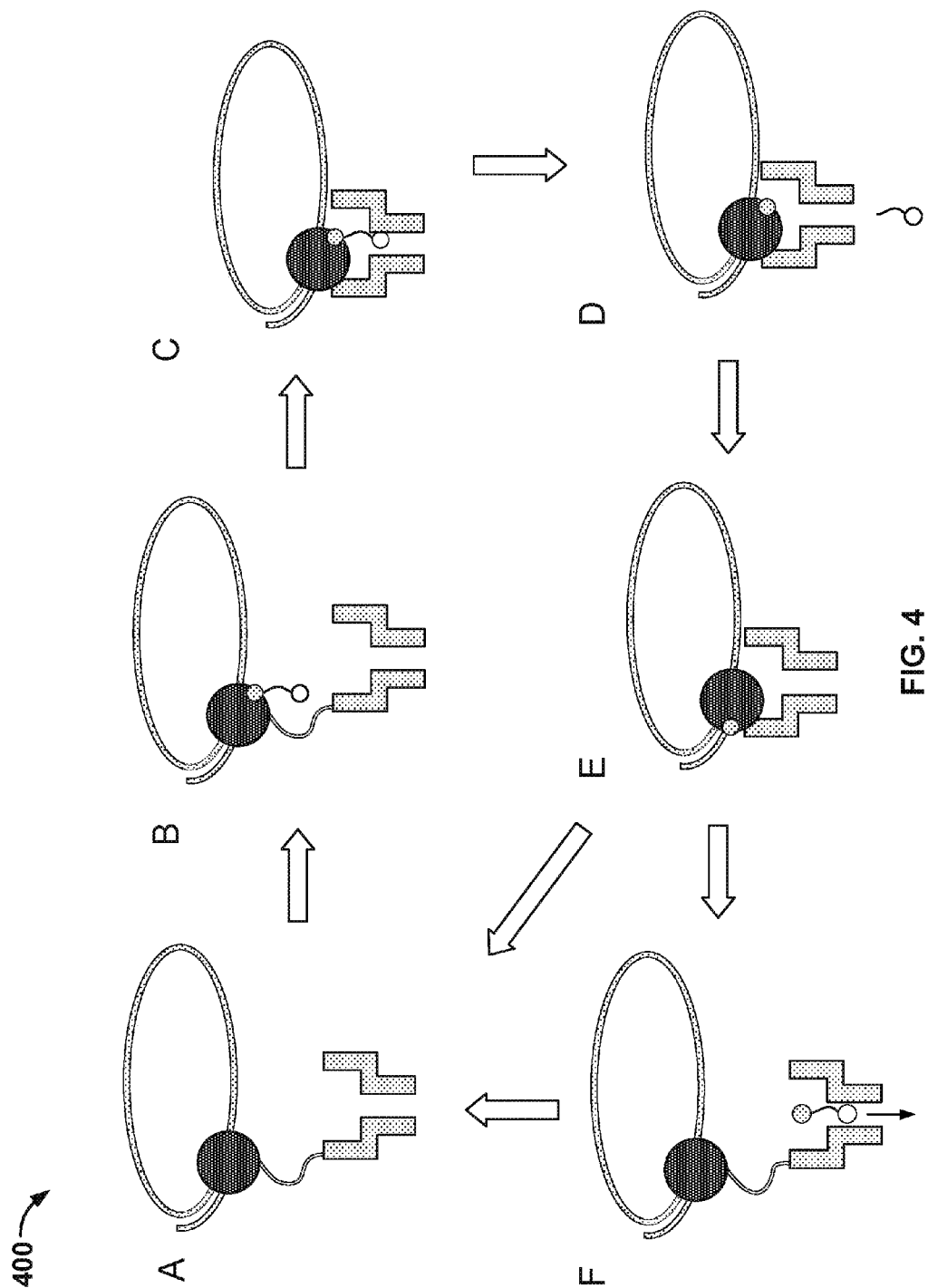
FIG. 4 illustrates an embodiment of a process 400 for nucleic acid sequencing with pre-loaded tags.

FIG. 4 illustrates an embodiment of a process 400 for nucleic acid sequencing with pre-loaded tags. At stage A, a tagged nucleotide (one of four different types: A, T, G, or C) is not associated with the polymerase. At stage B, a tagged nucleotide is associated with the polymerase. At stage C, the polymerase is in close proximity to the nanopore. The tag is pulled into the nanopore by an electrical field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage B.

Before the polymerase is docked to the nanopore, the conductance of the nanopore is ~300 pico Siemens (300 pS). At stage C, the conductance of the nanopore is about 60 pS, 80 pS, 100 pS, or 120 pS corresponding to one of the four types of tagged nucleotides. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structure, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

A fluid/gas delivery system for a sensor chip is disclosed. For example, a biological assay (e.g., nucleotide/nucleic acid sequencing) chip requires fluids and/or gases to be provided on the sensor chip, and a delivery system provides at least a portion of the materials required to perform the assay. In some embodiments, a plurality of selectable ports are arranged on a first assembly. Each selectable port is in communication with a separate channel. For example, each of the separate channels are connected to a different reagent, liquid, gas, waste container, etc. where material could be delivered/pushed or drawn/pulled. One of the separate channels may be connected to a biochip and material could be delivered/pushed or drawn/pulled to/from the biochip using this separate channel. A second assembly is movable in relation to the first assembly and the second assembly has a channel that is mechanically connectable to different ones of the plurality of ports on the first assembly by motion of the second assembly relative to the first assembly. A mechanical interface is configured to engage an actuator so that relative motion of the first assembly and the second assembly is affected by the actuator. For example, the second assembly includes a selection port that can be moved by an actuator/motor to be connected to any one of the plurality of selectable ports that are arranged on the first assembly. In this example, the selection port may be connected to only one port of the plurality of selectable ports of the first assembly at one time and the other selectable ports of the first assembly that are not connected to the selection port are sealed closed (e.g., sealed by the second assembly). In some embodiments, the selection port of the second assembly is connected to a pump and a chamber/channel that are utilized to deliver/push and/or draw/pull materials to/from the selected port of the plurality of selectable ports of the first assembly.

In some embodiments, any of the plurality of selectable ports can be selected to be connected to a two-way pump port. For example, a pump is configured to either draw or deliver fluid/gas from/to the two-way pump port. A chamber is connected to a first chamber port that is included in the plurality of selectable ports. For example, the first chamber port can be selected to connect to the two-way pump port. The chamber is also connected to a second chamber port. For example, the chamber includes a biochip and the first chamber port at least allows a reagent to enter the chamber and the second chamber port at least allows the reagent to exit the chamber after passing through the biochip in the chamber. A waste port is included in the plurality of ports. For example, a selection may be made to flow material to be discarded either through the second chamber port or to the waste port without passing through the second chamber port. For example, by having a two-way pump and a selectable waste port that allows waste to bypass the chamber, materials that ideally should not flow entirely through the chamber/biochip in an assay process may be discarded via the selectable waste port rather than a chamber port.

Figure 5:
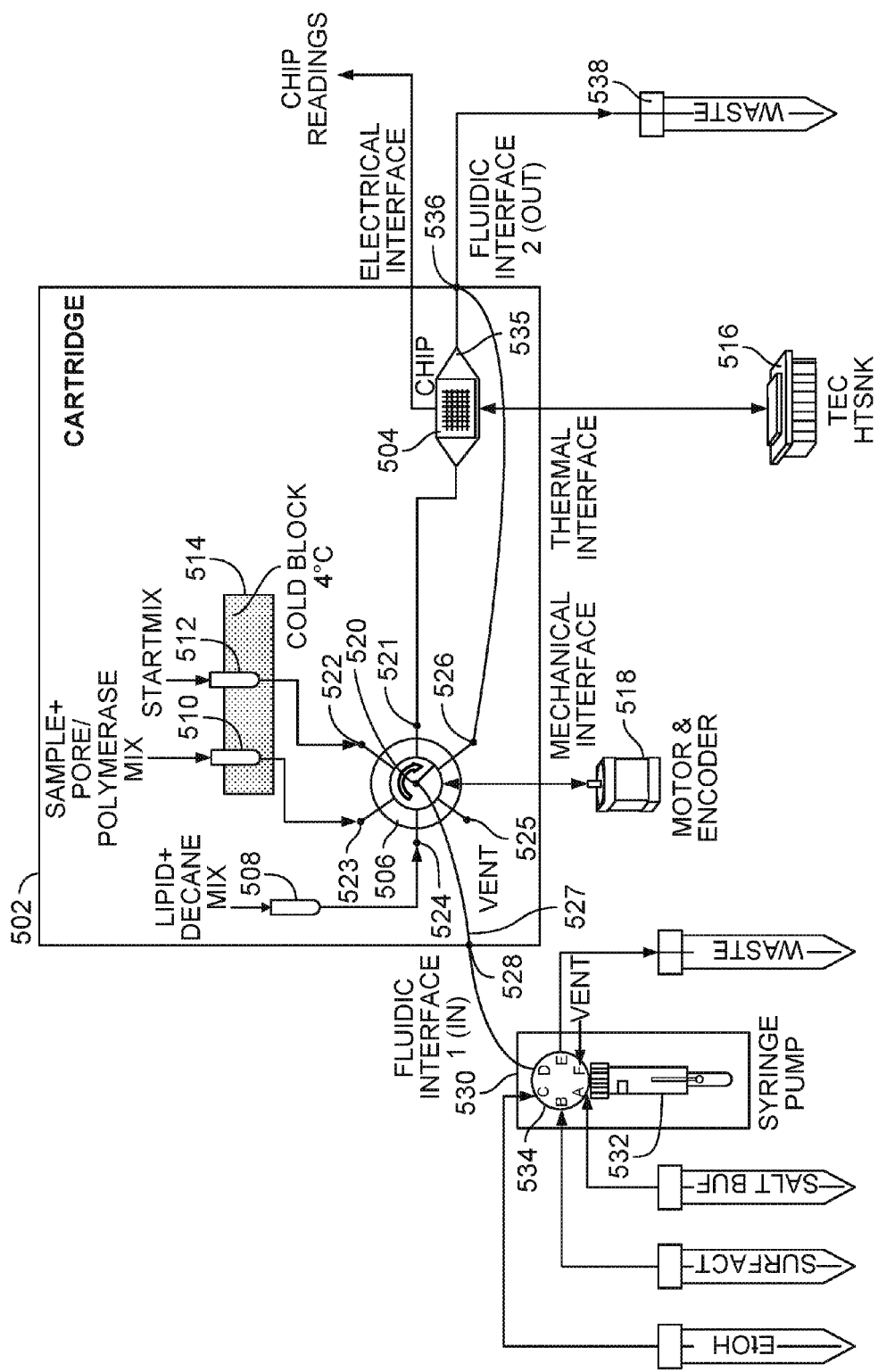
FIG. 5 is a schematic diagram illustrating an embodiment of at least a portion of a biological sensor system.

FIG. 5 is a schematic diagram illustrating an embodiment of at least a portion of a biological sensor system. For example, the biological sensor system is a nanopore-based nucleotide sequencing system.

The sensor system includes cartridge 502. Cartridge 502 engages with an instrument system, interfaces with the instrument system, and functions together with the instrument system to perform a biological assay (e.g., nanopore-based nucleotide sequencing). In FIG. 5, one or more of the components shown to be not included in cartridge 502 may be included on the instrument system. Cartridge 502 is removable from the instrument system and another cartridge may be engaged with the instrument system. By utilizing a removable cartridge, the components of the cartridge may be replaced quickly and easily on the instrument system without the need to clean and reuse the components of the cartridge. For example, the cartridge may be replaced for each different biological sample to be assayed by the instrument system.

Cartridge 502 includes biochip 504, radial valve 506, container 508, container 510 and container 512. Each of containers 508, 510 and 512 may hold a liquid, a reagent, a gas, a solid (e.g., suspended in liquid) and any other substance to be utilized in performing a biological measurement. For example, container 508 holds a lipid and decane mix, container 510 holds a sample and pore/polymerase mix, and container 512 holds a StartMix. Container 510 and container 512 are sensitive to temperature changes and thermal block 514 is thermally coupled to containers 510 and 512. For example, thermal block 514 provides thermal cooling to contents of container 510 and container 512. In some embodiments, thermal block 514 provides thermal heating and/or cooling to raise, lower, and/or maintain a temperature of contents of container 510 and container 512. In the example shown, thermal block 514 is not a part of cartridge 502 and is a part of the instrument system. Biochip 504 may be the nanopore-based sequencing chip described elsewhere in the specification. Biochip 504 is electrically connected/interfaced with the instrument system and electrical measurement data is read from biochip 504 and exported out of the biochip 504 to the instrument system for storage/analysis. For example, cartridge 502 includes a circuit board that provides electrical contact interfaces between biochip 504 and the instrument system. Biochip 504 is thermally coupled to the instrument system via a thermoelectric cooler (TEC)/heat sink assembly 516. The TEC/Heat sink assembly 516 allows the temperature of the biochip 504 to be controlled. For example the biochip and its fluid contents can be held at a constant temperature (e.g., warm or cold) and/or exposed to varying temperatures in a controlled manner (e.g., thermal cycling).

Radial valve 506 mechanically engages actuator/motor 518 of the instrument system. Actuator/motor 518 is separate from cartridge 502. Motor 518 actuates a movable assembly of radial valve 506 to select a desired port of radial valve 506. For example, motor 518 engages a movable assembly of radial valve 506 directly or indirectly via one or more gears, worm screws, or friction engagements (e.g., friction wheel).

Radial valve 506 includes central port 520 and selectable ports 521-526 that are arranged coaxially in a rotary configuration. Radial valve 506 may be rotated via actuator/motor 518 to select one of selectable ports 521-526 as the active/open port. The other not selected ports of selectable ports 521-526 may or may not be automatically sealed/closed when the selected port is selected. Materials may be passed between central port 520 and the selected port. For example, a fluid/gas passage channel is created between central port 520 and the selected port. Central port 520 is connected to interface 528 via a channel (e.g., tube). Interface port 528 is an interface of cartridge 502 where materials may enter/exit cartridge 502. Examples of interfaces of the cartridge include a needle septum, a flap valve or a ball displacement valve. Central port 520 is connected to pump 530 via interface 528. Pump 530 includes a syringe pump that may draw or push content into or out of pump chamber 532. Pump 530 includes a secondary radial value 534. In some embodiments, chamber 532 is a fluidic channel such as tubing. Pump 530 is a two-way pump that can deliver/push and draw/pull materials in to/out of pump chamber 532.

Radial valve 534 may be configured to connect pump chamber 532 to any of selectable ports A-F as shown in FIG. 5. Radial valve 534 may be rotated via an actuator/motor to select one of selectable ports A-F as the selected active/open port. The other not selected ports of selectable ports A-F are automatically sealed/closed when the selected port is selected. Liquid/gas may be passed between pump chamber 532 and the selected port of valve 534. Port A is connected to a salt buffer solution. Port B is connected to a surfactant solution. Port C is connected to ethanol. Port D is connected to central port 520 via interface 528. For example, when port D is selected on radial valve 534, pump 530 is able to deliver/push any material in pump chamber 532 to a selected port of radial valve 506 and pump 530 is able to pull any material from the selected port of radial valve 506 into chamber 532. Port E is connected to a waste container where content in chamber 532 can be discarded. Port F is connected to an air vent. For example, ambient air can be drawn into chamber 532 when port F is selected on radial valve 534. In an alternative embodiment, rather than utilizing two radial valves, a single radial valve on cartridge 502 is utilized. For example, valve 506 may include additional ports for additional reagents and central port 520 is connected to pump chamber 532 without another intervening radial valve.

In some embodiments, by delivering/pushing and drawing/pulling various materials to/from the ports of radial valve 534 and/or radial valve 506 using pump 530 in a configured sequence, a biological assay is performed using biochip 504. For example, a reagent to be pushed into chip 504 may be placed in chamber 532 by selecting one of selectable ports A-C on valve 534 connected to a desired reagent, pumping content of the selected port into chamber 532, then selecting port D on valve 534 and selecting port 521 on valve 506, and pushing the content of chamber 532 to chip 504. In another example, a reagent to be pushed into chip 504 may be placed in chamber 532 by selecting port D on valve 534 and selecting one of selectable ports 522-524 on valve 506 connected to the desired reagent, pumping content of the selected port into pump chamber 532, then selecting port 521 on valve 506 and pushing the content of chamber 532 to chip 504. In another example, a reagent to be pushed into chip 504 may be drawn out of chambers 508, 510 or 512 by selecting the corresponding port 524, 523 or 522, and selecting port D on valve 534. In this example, a reagent is drawn into fluid channel 527, but not past fluid interface 528 which keeps the reagent within the cartridge and does not contaminate surfaces outside of the cartridge (e.g. pump chamber 532). Port 521 can then be selected on valve 506, and the reagent can be pushed into the chip 504.

Often in the sequence, a material flowed on chip 504 needs to be discarded as a next material is flowed on chip 504. Interface 536 is an interface of cartridge 502 where waste materials to be discarded may exit cartridge 502. Material in the chamber of chip 504 may be pushed out of the chamber and into waste container 538 via chamber exit port 535 and interface 536. However in some cases, it may be desirable to be able to discard material without flowing the material to be discarded completely across chip 504 and out chamber port 535. In some embodiments, port 521 is selected on valve 506 and pump 530 pulls material out of the chamber of chip 504. Then port 526 is selected and the material to be discarded in pump chamber 532 is pushed out into waste container 538 via an alternative channel path that does not enter the chamber of chip 504 and does not include chamber port 535 yet still exits via interface port 536. Other materials pumped from other sources by pump 530 to be discarded may also be pushed into waste container 538 bypassing chip 504 via the alternative channel path. Examples of waste container 538 include a vented container, an expandable container, a one-way valve container, and an absorbent material filled container (e.g., to prevent flow back onto chip 504). In an alternative embodiment, waste container 538 is included in cartridge 502.

The embodiment shown in FIG. 5 is merely an example and has been simplified to illustrate the embodiment clearly. For example, the radial valves shown in FIG. 5 may include any number of selectable ports. Additional components not shown in FIG. 5 may also exist.

Figure 6:
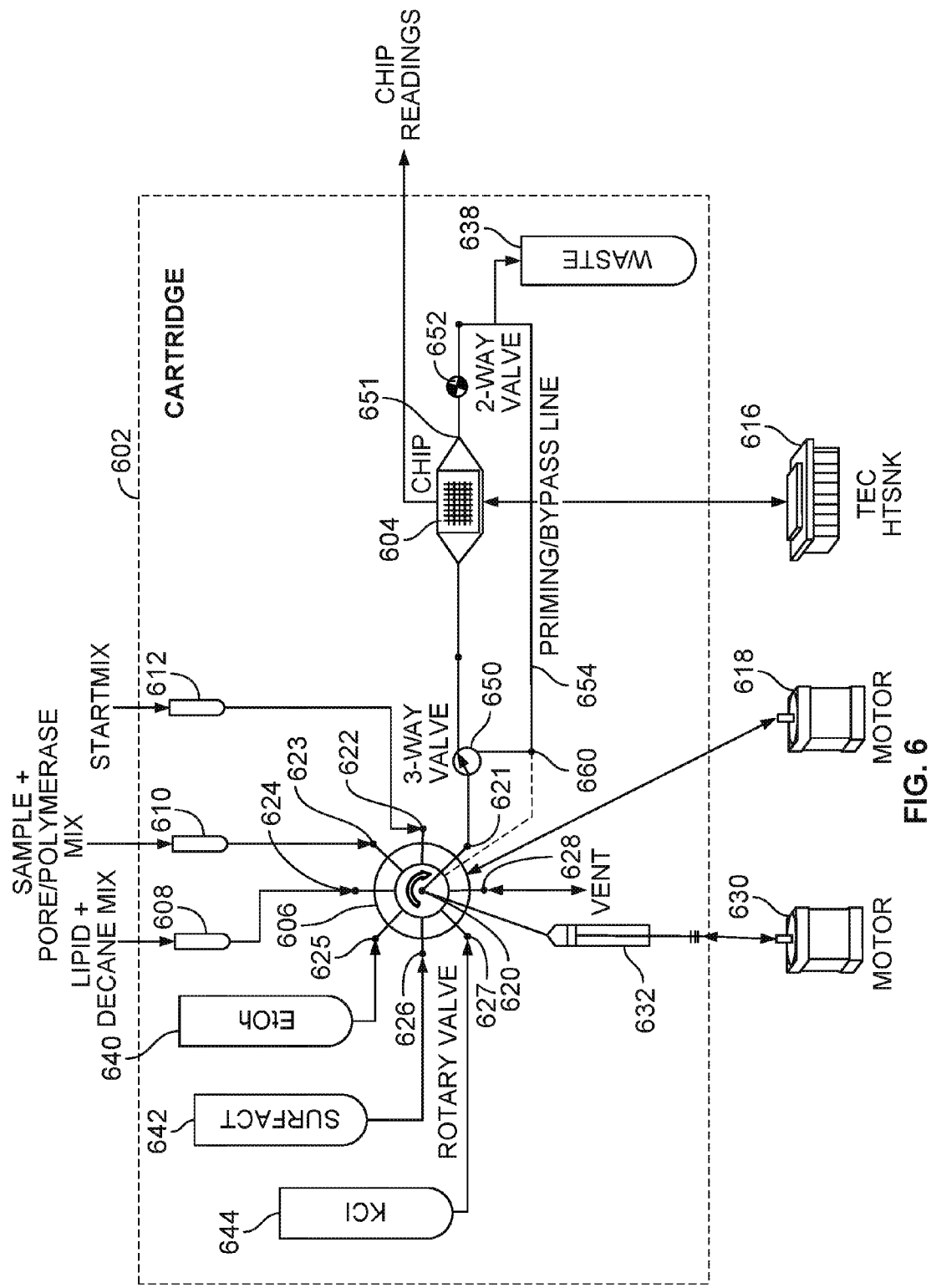
FIG. 6 is a schematic diagram illustrating another embodiment of at least a portion of a biological sensor cartridge system.

FIG. 6 is a schematic diagram illustrating another embodiment of at least a portion of a biological sensor cartridge system. For example, the biological sensor cartridge system is a nanopore-based nucleotide sequencing system.

The sensor system includes cartridge 602. Cartridge 602 engages with an instrument system, interfaces with the instrument system, and functions together with the instrument system to perform a biological assay (e.g., nanopore-based nucleotide sequencing). In FIG. 6, one or more of the components shown to be not included in cartridge 602 may be included on the instrument system. Cartridge 602 is removable from the instrument system and another cartridge may be engaged with the instrument system. By utilizing a removable cartridge, the components of the cartridge may be replaced quickly and easily on the instrument system without the need to clean and reuse the components of the cartridge. For example, the cartridge may be replaced for each different biological sample to be assayed by the instrument system.

Cartridge 602 includes biochip 604 in a chamber, radial valve 606, and containers 608, 610, 612, 640, 642, and 644. Each of containers 608, 610, 612, 640, 642 and 644 may hold a liquid, a reagent, a gas, a solid (e.g., suspended in liquid), and any other substance to be utilized in performing a biological measurement. For example, container 608 holds a lipid and decane mix, container 610 holds a sample and pore/polymerase mix, container 612 holds a StartMix, container 640 holds ethanol, container 642 holds a surfactant solution, and container 644 holds a salt buffer solution. In some embodiments, container 610 and container 612 are sensitive to temperature changes and a thermal block provides thermal heating and/or cooling to raise, lower, and/or maintain a temperature of contents of container 610 and container 612. Biochip 604 may be the nanopore-based sequencing chip described elsewhere in the specification. Biochip 604 is electrically connected/interfaced with the instrument system and electrical measurement data is read from biochip 604 and exported out of the biochip 604 to the instrument system for storage/analysis. For example, cartridge 602 includes a circuit board that provides an electrical contact interface between biochip 604 and the instrument system. Biochip 604 is thermally coupled to the instrument system via TEC/heat sink assembly 616. TEC/heat sink assembly 616 allows thermal energy of biochip 604 to be dissipated via assembly 616.

Radial valve 606 mechanically engages actuator/motor 618 of the instrument system. Actuator/motor 618 is separate from cartridge 602. Motor 618 actuates a movable assembly of radial valve 606 to select a desired port of radial valve 606. For example, motor 618 engages a movable assembly of radial valve 606 directly or indirectly via one or more gears, worm screws, or friction engagements (e.g., friction wheel).

Radial valve 606 includes central port 620 and selectable ports 621-628 that are arranged coaxially in a rotary configuration. Radial valve 606 may be rotated via actuator/motor 618 to select one of selectable ports 621-628 as the active/open port. The other not selected ports of selectable ports 621-628 are automatically sealed/closed when the selected port is selected. Selectable port 628 is connected to an air vent. For example, ambient air can be drawn into chamber 632 when port 628 is selected on radial valve 606. Materials may be passed between central port 620 and the selected port. For example, a fluid/gas passage channel is created between central port 620 and the selected port. Central port 620 is connected to pump chamber 632. In some embodiments, the pump chamber is located external to cartridge 602 and central port 620 is connected to the external pump chamber via an interface port of cartridge 602 connected to central port 620 via a channel (e.g., tube). Pump chamber 632 is a part of a two-way syringe pump that may draw or push content into or out of pump chamber 632. In some embodiments, pump chamber 632 is a fluidic channel such as tubing.

A piston of pump chamber 632 mechanically engages a moveable assembly of actuator/motor 630 of the instrument system directly or indirectly via one or more gears, worm screws, or friction engagements. The push/pull action of the syringe pump is controlled by actuating actuator/motor 630. Materials may be passed between pump chamber 632 and the selected port of valve 606. For example, material may be pushed into chamber 632 from a selected port of valve 606 and material in chamber 632 may be pushed out of chamber 632 to a selected port of valve 606.

In some embodiments, by delivering/pushing and drawing/pulling various materials to/from the ports of radial valve 606 using the pump of chamber 632 in a configured sequence, a biological assay is performed using biochip 604. For example, a reagent to be delivered/pushed into chip 604 may be placed in chamber 632 by selecting one of selectable ports 622-628 on valve 606 connected to a desired reagent/gas, pumping content of the selected port into pump chamber 632, then selecting port selecting port 621 on valve 606 and pushing the content of pump chamber 632 to chip 604.

Often in the sequence, a material flowed on chip 604 needs to be discarded as a next material is flowed across chip 604 to exit the chamber of 604. Material in the chamber of chip 604 may be pushed out of the chamber via chamber port 651 and into waste container 638. However in some cases, it may be desirable to be able to discard material without flowing the material to be discarded completely across chip 604 to exit via chamber port 651. In some embodiments, port 621 is selected on valve 606 and material on the chip is pumped into pump chamber 632, then pushed out into waste container 638 via bypass channel path 654 that does not enter the chamber of chip 604. Three-way valve 650 may be switched to either connect port 621 with only the chamber of chip 604 or with only bypass channel 654, as appropriate. In an alternative embodiment, rather than using three-way valve 650, the chamber of chip 604 is always connected to port 621 (e.g., without three-way valve 650) and a bypass selectable port on radial valve 606 (e.g., alternative embodiment shown as selectable port 660) is always connected to bypass channel 654 to allow a connection between pump chamber 632 and waste container 638 without passing through the chamber of chip 604 when the bypass selectable port is selected. Other materials pumped from other sources (e.g., during initial priming) by the pump of chamber 632 to be discarded may also be pushed into waste container 638 via bypass channel 654. Examples of waste container 638 include a vented container, an expandable container, a one-way valve container, and an absorbent material filled container. Two-way valve 652 may be configured to switch between allowing or not allowing flow between its connected channels. By opening valve 652, material in the chamber of chip 604 may be directly pushed out into waste container 638. By closing valve 652, backflow on to chip 604 may be prevented when pushing waste into container 638 via bypass channel 654 or when waste content leaks out of waste container 638. The ability to close valve 652 may also enable the pump to pressurize the fluid or gas on chip 604. In some embodiments, valve 652 is optional. In an alternative embodiment, valve 652 is a one-way valve.

The embodiment shown in FIG. 6 is merely an example and has been simplified to illustrate the embodiment clearly. For example, the radial valves shown in FIG. 6 may include any number of selectable ports. Additional components such as other valves not shown in FIG. 6 may also exist. In some embodiments, linear valve 700 is included in cartridge 502 of FIG. 5. In some embodiments, linear valve 700 is included in cartridge 602 or FIG. 6.

Figure 7A:
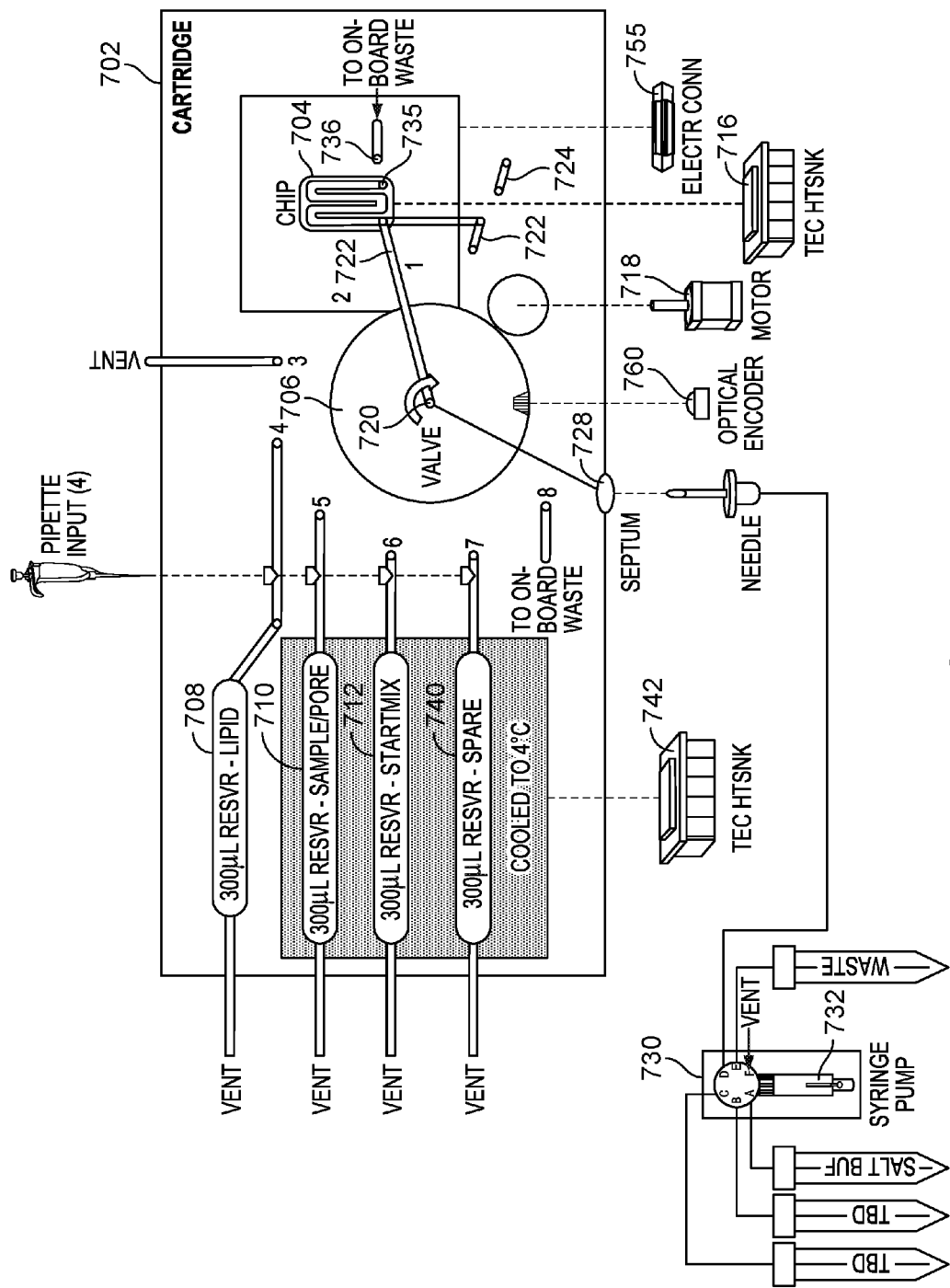
FIGS. 7A-7C are schematic diagrams illustrating another embodiment of at least a portion of a biological sensor cartridge system.
Figure 7B:
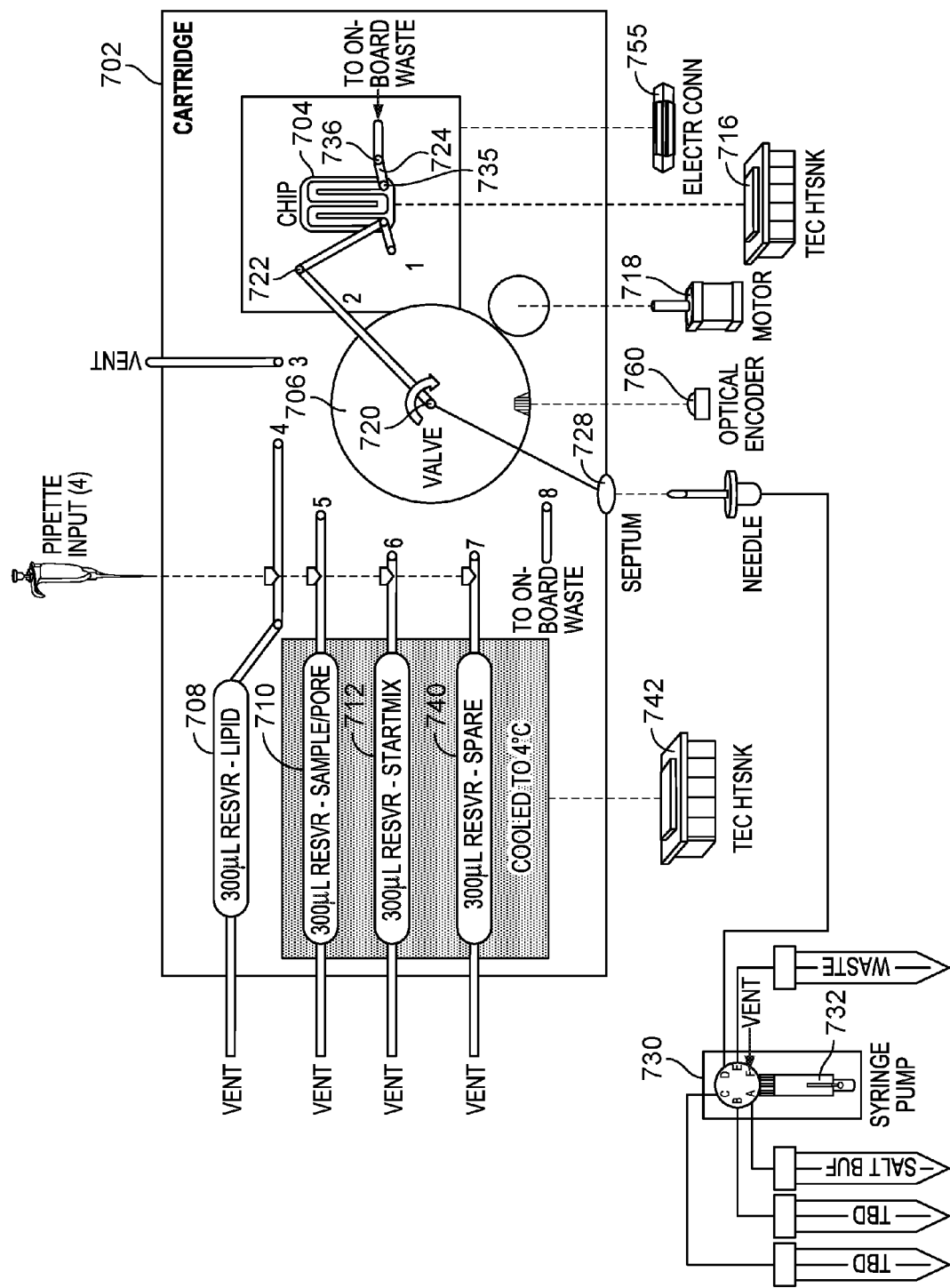
Figure 7C:
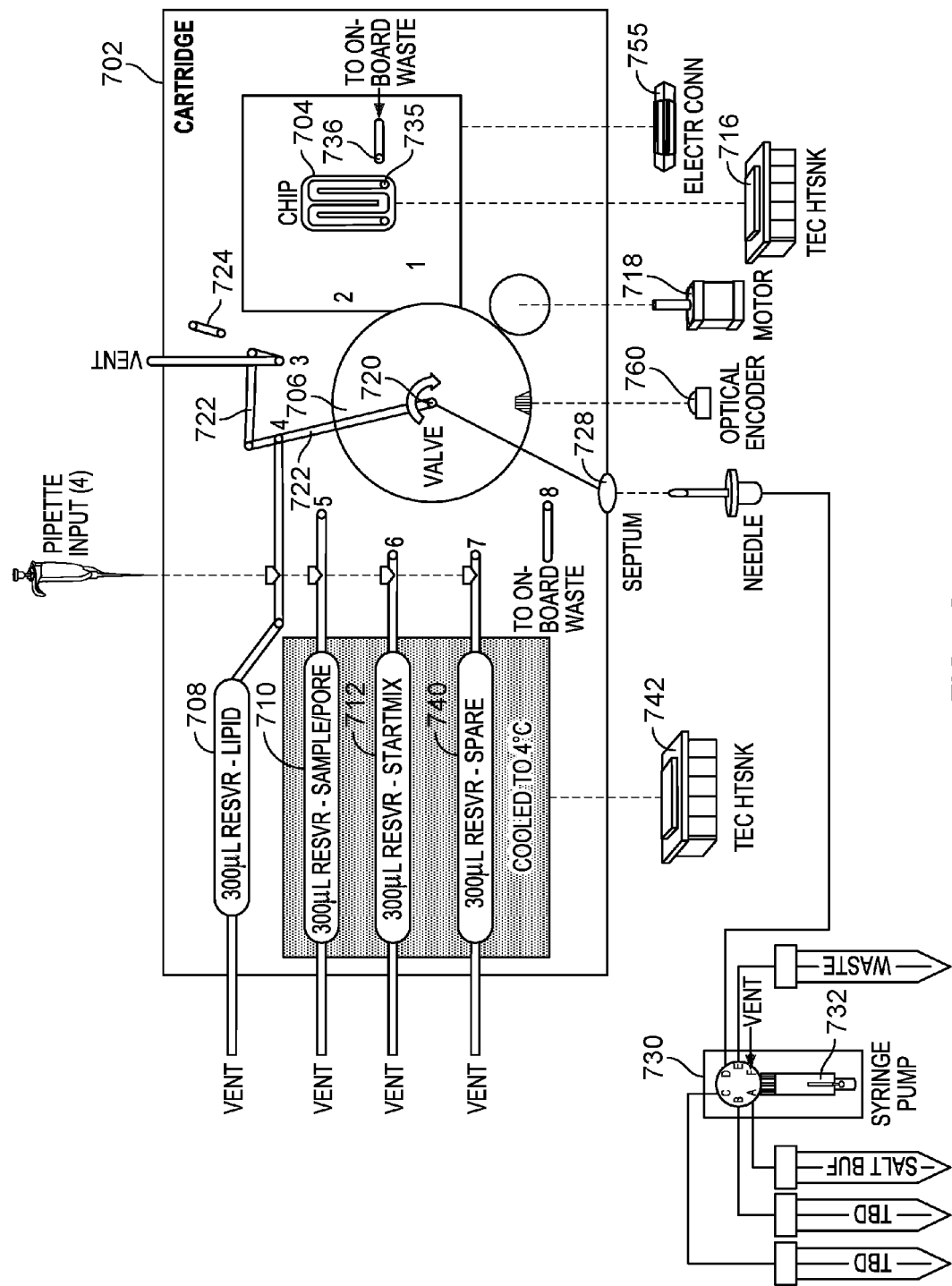

FIGS. 7A-7C are schematic diagrams illustrating another embodiment of at least a portion of a biological sensor cartridge system. For example, the biological sensor cartridge system is a nanopore-based nucleotide sequencing system.

The sensor system includes cartridge 702. Cartridge 702 engages with an instrument system, interfaces with the instrument system, and functions together with the instrument system to perform a biological assay (e.g., nanopore-based nucleotide sequencing). The bottom side of cartridge 702 may expose electrical contacts that allow electrical connection between one or more electrical components of cartridge 702 and the instrument system to be engaged with cartridge 702. The electrical contacts of the cartridge electrically interfaces with the instrument system via electrical connector 755. Cartridge 702 is removable from the instrument system and another cartridge may be engaged with the instrument system. By utilizing a removable cartridge, the components of the cartridge may be replaced quickly and easily on the instrument system without the need to clean and reuse the components of the cartridge. For example, the cartridge may be replaced for each different biological sample to be assayed by the instrument system.

Cartridge 702 includes biochip 704, radial valve 706, and containers 708, 710, 712 and 740 that are vented. Each of containers 708, 710, 712 and 740 may hold a liquid, a reagent, a gas, a solid (e.g., suspended in liquid), and any other substance to be utilized in performing a biological measurement. For example, container 708 holds a lipid and decane mix, container 710 holds a sample and pore/polymerase mix, container 712 holds a StartMix and container 740 is a reserved spare container. In some embodiments, at least container 710 and container 712 are sensitive to temperature changes and TEC/heat sink assembly 742 provides thermal heating and/or cooling to raise, lower, and/or maintain a temperature of contents of container 710 and container 712. Containers 708, 710, 712 and 740 are each connected to a different selectable port of radial valve 706. The channel paths connecting each container to a corresponding selectable port includes a pipette input that can be utilized to deliver material to the corresponding container and/or selectable port.

Biochip 704 may be the nanopore-based sequencing chip described elsewhere in the specification. Biochip 704 is electrically connected/interfaced with the instrument system via electrical connector 755 and electrical measurement data is read from biochip 704 and exported out of the biochip 704 to the instrument system for storage/analysis. Biochip 704 is thermally coupled to the instrument system via TEC/heat sink assembly 716. TEC/heat sink 716 allows thermal energy of biochip 704 to be dissipated via assembly 716.

Radial valve 706 mechanically engages actuator/motor 718 of the instrument system. Actuator/motor 718 is separate from cartridge 702. Motor 718 actuates a movable assembly of radial valve 706 to select one or more desired port of radial valve 706. For example, motor 718 engages a movable assembly of radial valve 706 directly or indirectly via one or more gears, worm screws, or friction engagements (e.g., friction wheel).

Radial valve 706 includes central port 720 and can be placed in any one of shown selectable positions 1-8 that are arranged coaxially in a rotary configuration. Radial valve 706 is rotated via actuator/motor 718 to select one of selectable positions 1-8. Positions 3-6 each correspond to a different selectable port that can be selected as the connected active/open port. The other not selected ports are automatically sealed/closed when the selected port is selected. Using positions 1 and 2 on radial valve 706, a direct connection between outlet port 735 of the chamber of chip 704 and port 736 connected to a waste container is controlled in addition to controlling a separate direct connection between central port 720 and the inlet port of the chamber of chip 704. In some embodiments, by allowing a single selectable valve to control a connection that does not directly involve its central port, a more efficient cartridge design may be achieved due to the multiple functions being performed by the selectable valve. For example, rather using valve 652 of FIG. 6, a single selectable valve such as valve 706 may be utilized to perform the functions of both radial valve 606 and valve 652 of FIG. 6.

The exact position of radial valve 706 is determined using optical encoder 760. For example, by reading/detecting a pattern on a moveable assembly of radial valve 706, optical encoder 760 converts the detected pattern corresponding to a specific position of the moveable assembly to an electrical signal/code that can be utilized to determine the specific position. In an alternative embodiment, rather than utilizing an optical encoder, a known "home" position of the radial valve is identified and an open loop control is utilized to rotate the radial valve a controlled amount (e.g., specified number of degrees). Channel 722 of radial valve 706 connects central port 720 to the selectable port (e.g., channel 722 has multiple selection ports as shown by circles on channel 722). When a moveable assembly of valve 706 is rotated, channel 722 is physically rotated together. In addition to channel 722, channel 724 is also moved when the moveable assembly of valve 706 is rotated. However, channel 724 is not directly connected to central port 720.

FIG. 7A shows radial valve 706 in position "1." In this position, central port 720 is connected to a selectable port that is connected to the inlet port (e.g., two-way port) of the chamber of chip 704, allowing materials to be passed between central port 720 and the chamber of chip 704. However, channel 724 does not connect any ports in position "1." Thus, chamber outlet port 735 of the chamber of chip 704 is sealed and not connected to port 736 of the waste container. This may allow chip 704 and contents of the chamber to be pressurized. FIG. 7B shows radial valve 706 in position "2." In this position, channel 722 still connects central port 720 with the selectable port that is connected to the inlet port of the chamber of chip 704, allowing materials to be passed between central port 720 and the chamber of chip 704. However, channel 724 now connects chamber outlet port 735 of the chamber of chip 704 with port 736 of the waste container, allowing waste to flow from the chip chamber to the waste container. FIG. 7C shows radial valve 706 in position "3." In this position, channel 722 connects central port 720 with the selectable port that is connected to an air vent. Channel 724 does not connect any ports in position "3."

Central port 720 is connected to interface 728 via a channel (e.g., tube). Interface port 728 is an interface of cartridge 702 where materials may enter/exit cartridge 702. In the example shown, a needle septum is utilized as the interface port. Central port 720 is connected to pump 730 via interface 728. Pump 730 includes a syringe pump that may draw or push content into or out of pump chamber 732. Pump 730 includes a secondary radial value. In some embodiments, chamber 732 is a fluidic channel such as tubing. Pump 730 is a two-way pump that can deliver/push and draw/pull materials in to/out of pump chamber 732. In some embodiments, pump 730 functions in a similar manner as pump 530 of FIG. 5. Position "8" of radial valve 706 corresponds to a selection of a bypass waste selectable port that allows a connection between central port 720 and a waste container without passing through the chamber of chip 704 when the bypass waste selectable port is selected.

Figure 8A:
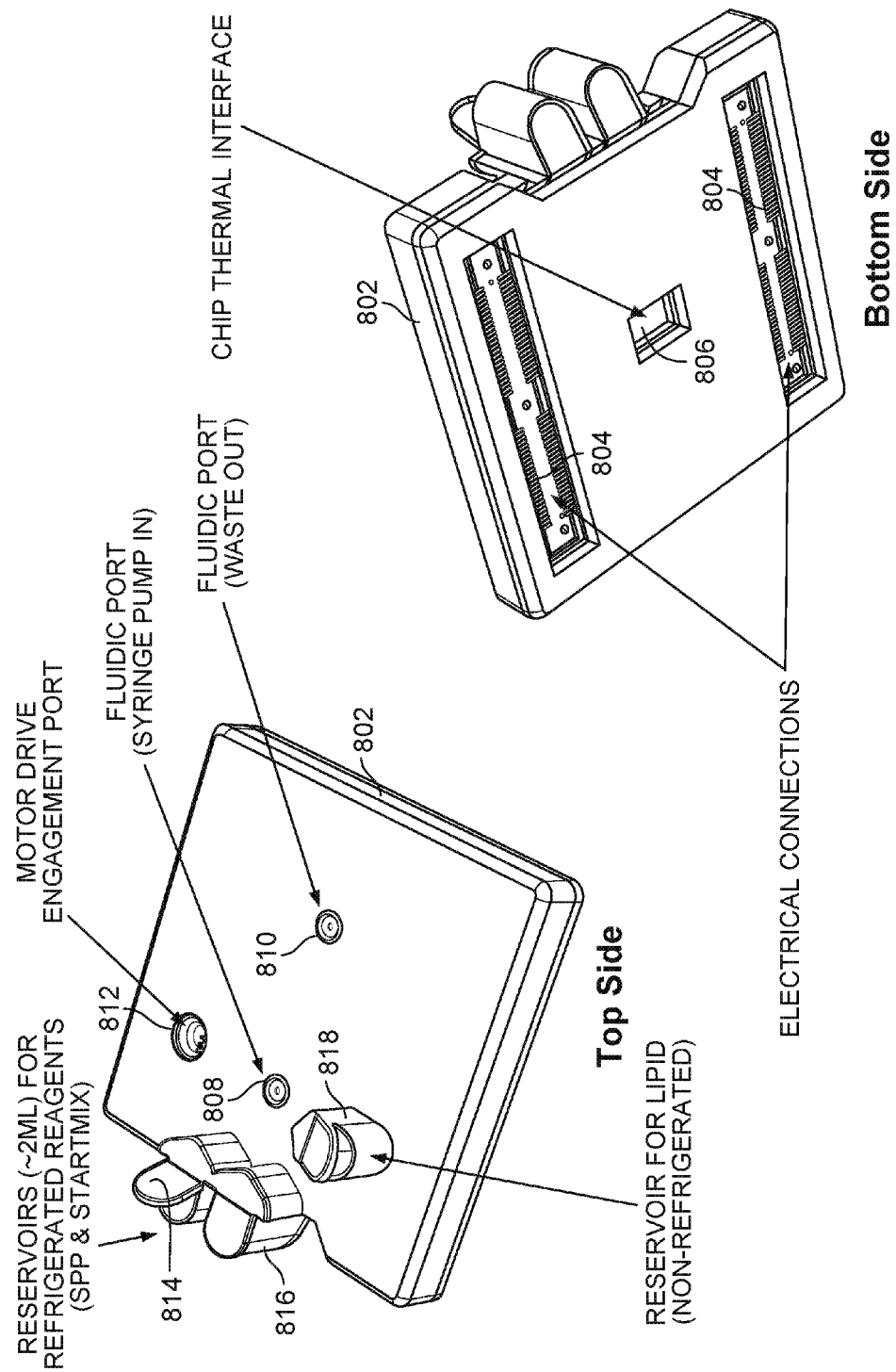
FIG. 8A is a diagram illustrating an embodiment of a cartridge.

FIG. 8A is a diagram illustrating an embodiment of a cartridge. In some embodiments, cartridge 802 is cartridge 502 of FIG. 5. In some embodiments, cartridge 802 shows at least a portion of features of cartridge 602 of FIG. 6 and/or cartridge 702 of FIG. 7.

The bottom side of cartridge 802 exposes electrical contacts 804. Electrical contacts 804 allow electrical connection between one or more electrical components of cartridge 802 and an instrument system to be engaged with cartridge 802. For example, electrical data (e.g., electrical measurement/reading data) of the biochip may be accessed/provided/received via electrical contacts 804 by the instrument system to determine a result of a biological assay. In some embodiments, electrical contacts 804 are contacts of a circuit board included in cartridge 802 and the circuit board is electrically connected to a biochip.

Thermal chip interface 806 provides a thermal interface where a heat sink (e.g., heat sink 516 of FIG. 5 or heat sink 616 of FIG. 6) can be thermally coupled to a biochip included in cartridge 802. For example, the heat sink allows thermal energy of the biochip to be dissipated via the heat sink. The heat sink may be a part of the instrument system that receives cartridge 802. Cartridge 802 includes interface port 808 and interface port 810. In some embodiments, interface port 808 is interface port 528 of FIG. 5. In some embodiments, interface port 808 is connected to a central port of a radial valve (e.g., connected port 520 of FIG. 5 or port 620 of FIG. 6) and/or a syringe pump. In some embodiments, interface port 810 is interface port 536 of FIG. 5. In some embodiments, interface port 810 is a waste port. Drive engagement port 812 is configured to engage with an actuator/motor to operate a selectable valve. For example, a selection of a selected valve among a plurality of selectable valves is performed by mechanically actuating an engagement mechanism (e.g., gear) exposed in motor drive engagement port 812. In some embodiments, motor drive engagement port 812 is utilized to select a selectable port of a radial valve (e.g., radial valve 506 of FIG. 5 or valve 606 of FIG. 6). In some embodiments, motor drive engagement port 812 is utilized to select a selectable port of a linear valve (e.g., linear valve 700 of FIG. 7).

Cartridge 802 includes thermally controlled containers 814 and 816. Container 818 is not to be thermally controlled. Containers 814, 816, and 818 may hold a liquid, a reagent, a gas, a solid (e.g., suspended in liquid), and any other substance to be utilized in performing a biological measurement. For example, container 814 holds a StartMix and container 816 holds a sample and pore/polymerase mix and container 818 holds a lipid and decane mix. Contents of containers 814, 816, and 818 are connected to selectable ports of a selectable valve via separate channels and the contents of the containers may be drawn for use during a biological assay via the corresponding selectable valve. Containers 814 and 816 may be thermal-controlled using a thermal block (e.g., thermally controlled using refrigerant, ice, Freon, thermal-electric, etc.) that surrounds at least a portion of containers 814 and 816 to reduce and/or maintain a temperature of its contents (e.g., via thermal conduction through walls of containers 814 and 816). In some embodiments, a thermal conductive material probe (e.g., metal rod) is placed within container 814 and/or container 816 and the probe is thermal-controlled (e.g., immersion cooled/heated via an external cool/heat source thermally coupled to the probe (e.g., probe extends through cap of the container such that the probe is partly immersed in contents of the container and partly exposed outside the container where the external thermal source may be coupled)).

Figure 8B:
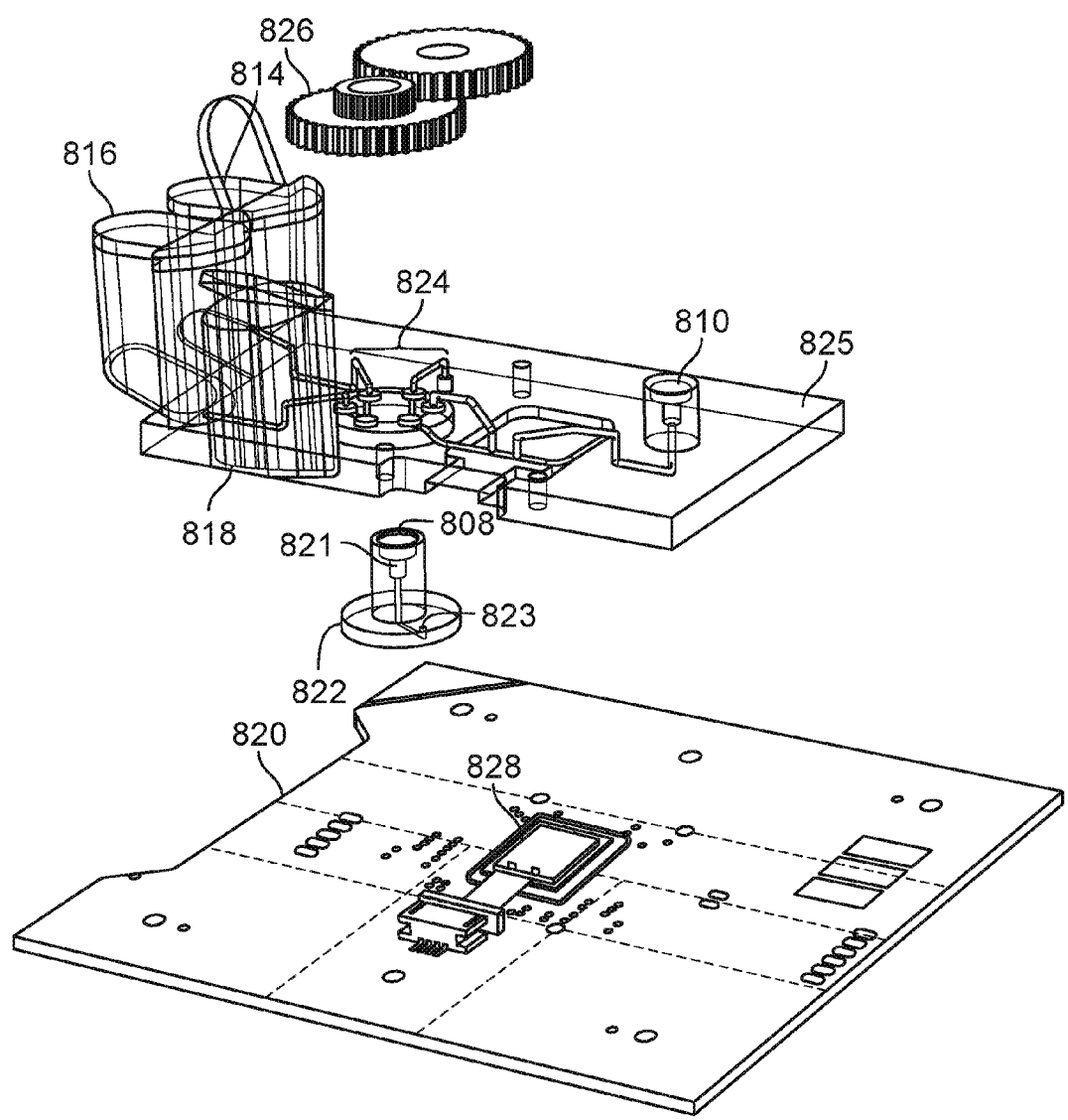
FIG. 8B is a diagram illustrating an embodiment of at least a portion of internal components of a cartridge.

FIG. 8B is a diagram illustrating an embodiment of at least a portion of internal components of a cartridge. In some embodiments, one or more components shown in FIG. 8B are included cartridge 502 of FIG. 5, cartridge 702 of FIG. 7 and/or cartridge 602 of FIG. 6.

The cartridge includes circuit board 820. Circuit board 820 is electrically coupled to biochip 828. In various embodiments, biochip 828 is biochip 504 of FIG. 5 and/or biochip 604 of FIG. 6. The bottom side of circuit board 820 includes electrical contacts 804 shown in FIG. 8A. The cartridge of FIG. 8B includes a radial valve. The radial valve comprises a port selector assembly 822. Selectable ports 824 are arranged coaxially in a rotary configuration on body assembly 825 that remains stationary while selector assembly 822 is rotated to select one of selectable ports 824 as the selected connected port. For example, port selector assembly 822 may be rotated using an external actuator/motor to select one of selectable ports 824 as a selected port that will be connected via a channel on selector assembly 822 to central port 821.

Central port 821 is connected to interface port 808 where a two-way pump may be coupled. By rotating selector assembly 822 to a specific location on assembly 825 where connector port 823 becomes aligned with a desired one of selectable ports 824, a channel between the selected port and central port 821 is established while the other not selected ports of selectable ports 824 become sealed by selector assembly 822. In some embodiments, selector assembly 822 includes a mechanical interface (e.g., gear) that is included in or mechanically coupled to gears 826. Selector component 822 is rotated using gears 826 that are mechanically engaged with an actuator via engagement port 812 shown in FIG. 8A.

Figure 8C:
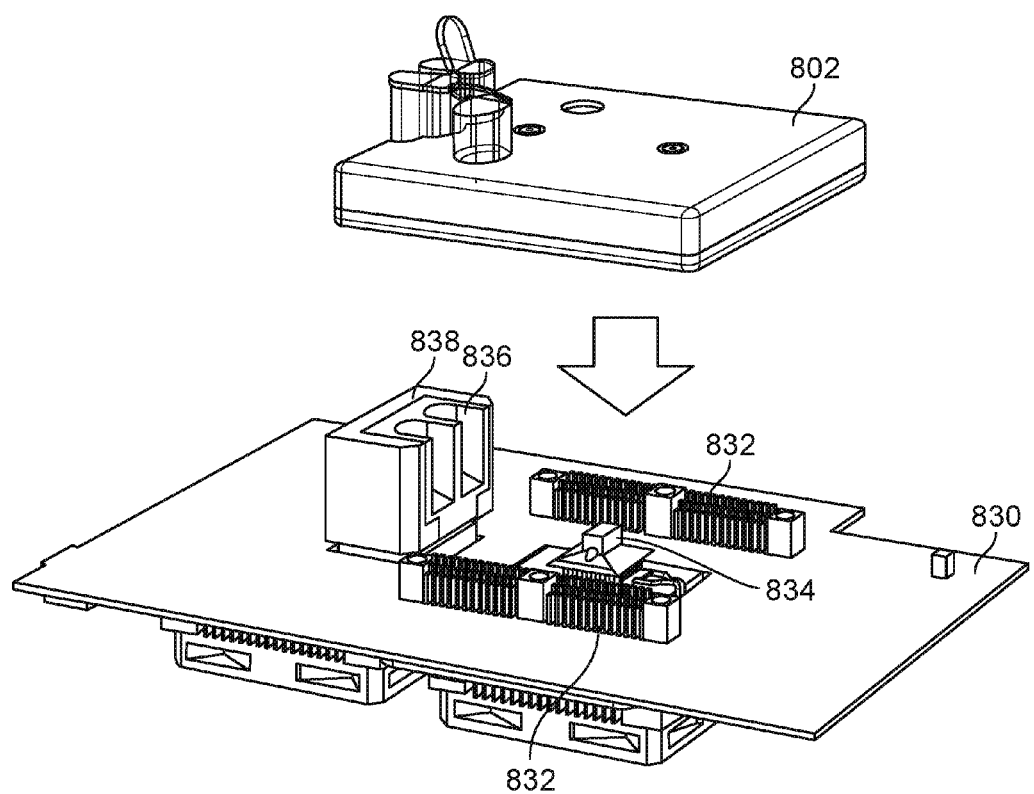
FIG. 8C is a diagram illustrating an embodiment of a cartridge and an instrument system that engages the cartridge.

FIG. 8C is a diagram illustrating an embodiment of a cartridge and an instrument system that engages the cartridge. In some embodiments, cartridge 802 is cartridge 502 of FIG. 5. In some embodiments, cartridge 802 shows at least a portion of features of cartridge 602 of FIG. 6 and/or cartridge 702 of FIG. 7.

Cartridge 802 may be pushed down and received by instrument 830 to engage cartridge 802 with instrument 830. Cartridge 802 may be removed from instrument 830 after use and another cartridge may be engaged with instrument 830 for a different sample. In some embodiments, instrument 830 is at least a portion of a system utilized to perform a biological assay (e.g., nucleotide sequencing). Instrument 830 includes male connectors 832 that can be coupled with electrical contacts 804 shown in FIG. 8A. Electrical connections between a biochip included in cartridge 802 and one or more electrical components of instrument 830 are established via male connectors 832. Instrument 830 includes heat sink 834. Heat sink 834 can be thermally coupled to a biochip via thermal interface 806 of FIG. 8A. Examples of heat sink 834 include heat sink 516 of FIG. 5 and heat sink 616 of FIG. 6. Thermal block 836 (e.g., cold block) of instrument 830 is configured to surround at least a portion of containers 814 and 816 and provide a thermal source to thermally control (e.g., cool/heat) the contents of containers 814 and 816. Thermal block 836 is surrounded by thermal insulation 838 to maintain thermal energy of thermal block 836. In some embodiments, when cartridge 802 is engaged with instrument 830, cartridge 802 and instrument 830 are mechanically clamped together using one or more clamps.

Figure 9:
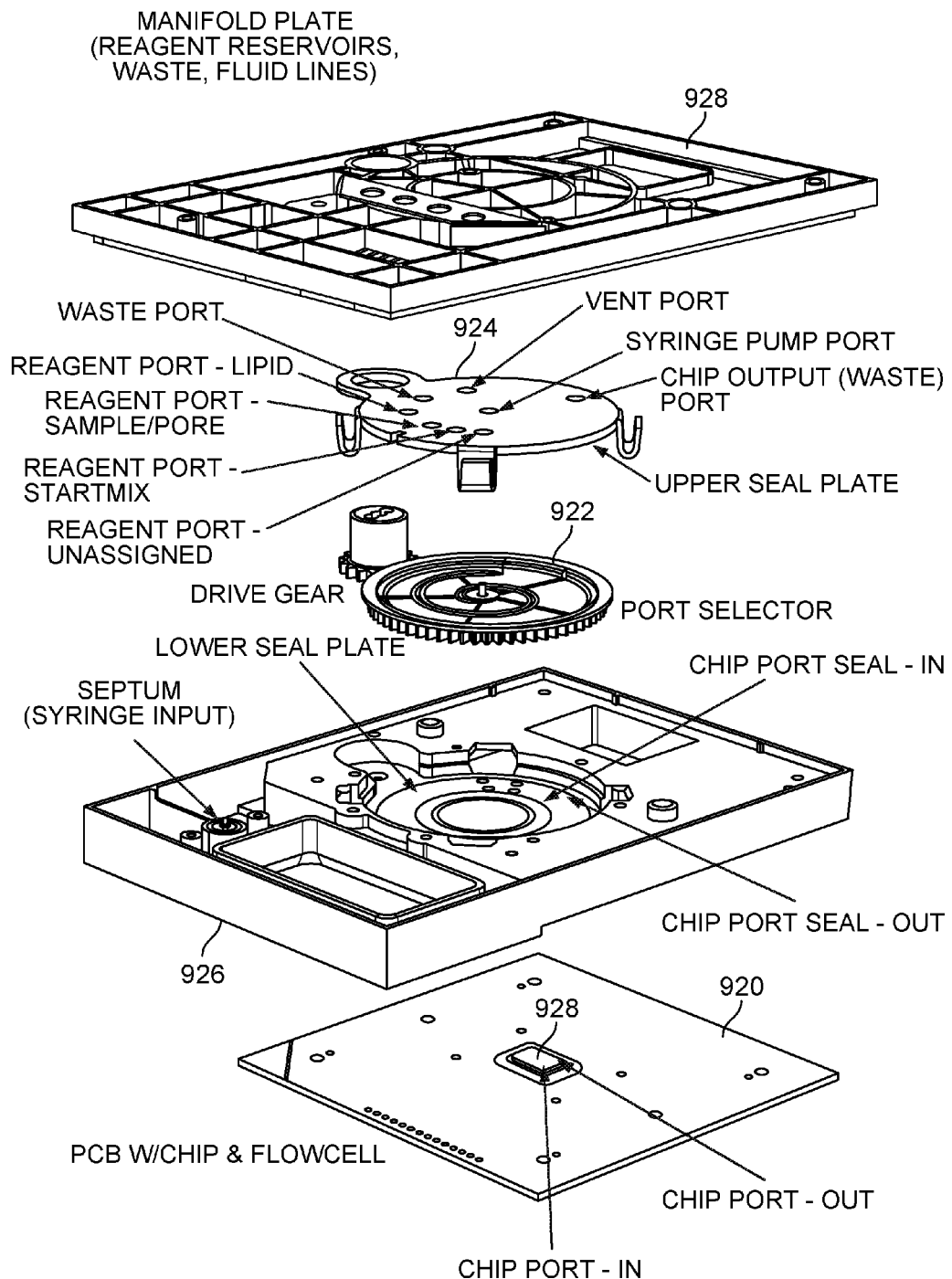
FIG. 9 is a diagram illustrating another embodiment of at least a portion of internal components of a cartridge.

FIG. 9 is a diagram illustrating another embodiment of at least a portion of internal components of a cartridge. In some embodiments, the cartridge components shown in FIG. 9 are included in cartridge 702 of FIG. 7. In some embodiments, one or more of the cartridge components shown in FIG. 9 are included in cartridges 502 and/or 602 of FIGS. 5 and 6.

The cartridge includes circuit board 920. Circuit board 920 is electrically coupled to biochip 928. In various embodiments, biochip 928 is biochip 504 of FIG. 5, biochip 604 of FIG. 6 and/or biochip 704 of FIG. 7. The cartridge of FIG. 9 includes a radial valve. The radial valve comprises port selector assembly 922. Selectable ports are engaged on both sides of port selector assembly 922. Port selector assembly 922 selector seals and connects ports on both the top (e.g., going to the reagents via upper seal plate assembly 924) and bottom (e.g., going to the chip via lower seal plate assembly 926) of assembly 922. Port selector assembly 922 is positioned on top of chip 928 and is oriented such that an inlet of the chamber of the chip is positioned along an inner ring of ports on lower seal plate assembly 926 and the outlet of the chamber of the chip is positioned along an outer ring of ports on lower seal plate assembly 926. By rotating selector assembly 922 to specific locations on assemblies 924 and 926 where connector ports on selector assembly 922 becomes aligned with desired connector port(s) on upper seal plate assembly 924 and lower seal plate assembly 926, one or more desired channel connections are created while other connector ports may be sealed. For example, in one position, both inlet and outlet ports of the chamber of the chip are open, allowing fluid flow through the chip. In a second position the inlet is open, but the outlet is blocked, allowing the fluid inside the chip to be pressurized (e.g., part of lipid bilayer formation protocol). In some embodiments, port selector assembly 922 includes channels 722 and 724 of FIG. 7. Manifold plate assembly 928 includes containers/reservoirs, a waste container and/or channels. Selector assembly 922 includes a mechanical interface (e.g., gear) that is included in or mechanically coupled to drive gears of an actuator/motor. Upper seal plate assembly 924 and lower seal plate assembly 926 remain stationary while selector assembly 922 is rotated to a desired position.

Figure 10:
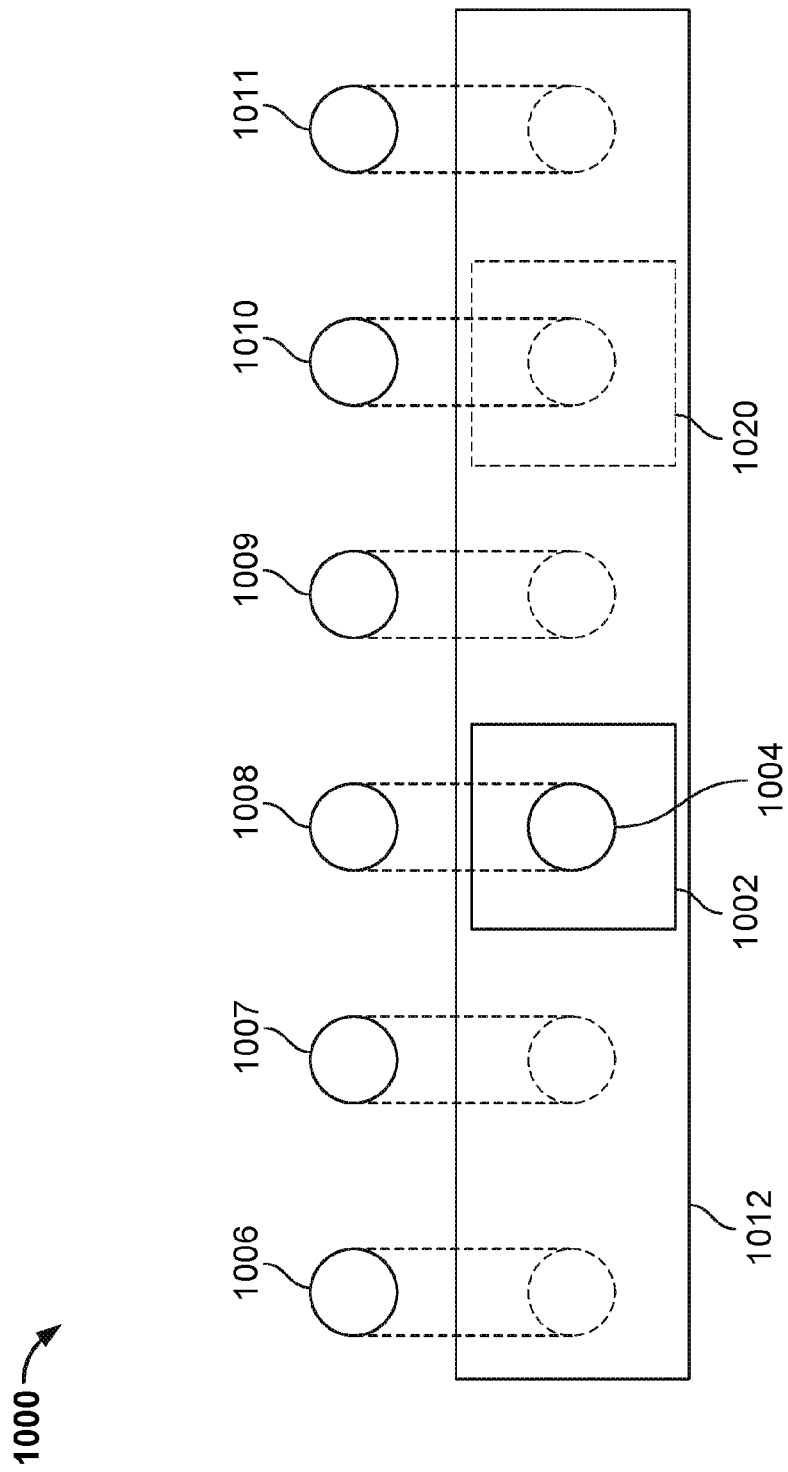
FIG. 10 is a schematic diagram illustrating an embodiment of a linear valve.

FIG. 10 is a schematic diagram illustrating an embodiment of a linear valve. In some embodiments, rather than utilizing radial valve 506 of FIG. 5, radial valve 606 of FIG. 6, or radial valve 706 of FIG. 7, linear valve 1000 may be utilized in its place. Selector assembly 1002 moves along track 1012 to select one of selectable ports 1006-1011 to be connected to central port 1004. For example, a motor moves selector 1002 along track 1012 to one of a plurality of specific locations on a stationary assembly that each correspond to one of selectable ports 1006-1011. At each location of track 1012 of the stationary assembly that corresponds to a specific selectable port, an opening connected to the specific selectable port is able to be connected to central port 1004 when selector 1002 is moved to the specific location corresponding to the specific selectable port. In the example shown, selector 1002 is at a location of track 1012 corresponding to selectable port 1008. In another example, selector assembly 1002 may be moved to the position outlined as 1020 to select port 1010. The motor may be a part of an instrument while linear valve 1000 is a part of a separate removable cartridge that engages with the instrument. Selector assembly 1002 may be moved by the motor directly or indirectly via one or more gears, worm screws, pistons, friction engagements, or belts.

When one of selectable ports 1006-1011 is selected by selector 1002 as the active/open port (e.g., selector 1002 is moved to a location on track 1012 corresponding to the selected port), other not selected ports of selectable ports 1006-1011 are automatically sealed/closed when the selected port is selected. Materials may be passed between central port 1004 and the selected port. For example, a fluid/gas passage channel is created between central port 1004 and the selected port. Central port 1004 may be connected to a syringe pump (e.g., connected to pump 530 of FIG. 5, pump 730 of FIG. 7 or to pump of chamber 632 of FIG. 6). Each of selectable ports 1006-1011 may be connected to different reagents, gasses, vents, waste containers, cleaning solutions, biological samples, channels, etc. via separate corresponding channels. For example, materials/components utilized in performing a biological assay are connected to the selectable ports. The number of ports and/or the shape of the linear valve shown in FIG. 10 is merely an example. Any number of ports and selectable valve shapes may exist in various embodiments.

Figure 11:
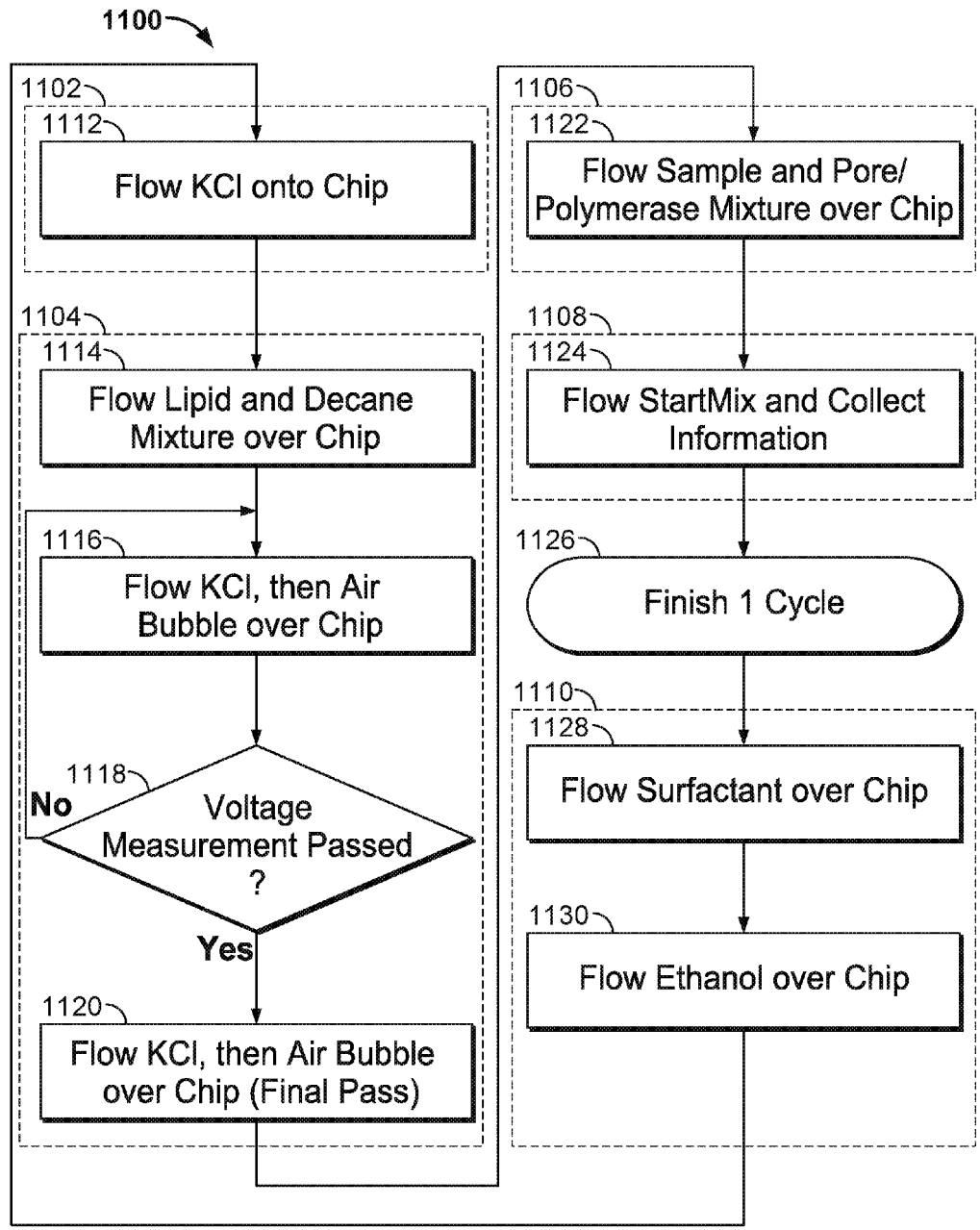
FIG. 11 is a flowchart illustrating an embodiment of a process for flowing different types of materials (e.g., liquids or gases) through the cells of a nanopore-based sequencing biochip during different phases of the biochip operation.

FIG. 11 is a flowchart illustrating an embodiment of a process for flowing different types of materials (e.g., liquids or gases) through the cells of a nanopore-based sequencing biochip during different phases of the biochip operation. The nanopore-based sequencing biochip operates in different phases, including an initialization and calibration phase (phase 1102), a membrane formation phase (phase 1104), a nanopore formation phase (phase 1106), a sequencing phase (phase 1108), and a cleaning and reset phase (phase 1110). In some embodiments, the biochip of FIG. 11 includes cell 100 of FIG. 1. In some embodiments, the biochip of FIG. 11 is biochip 504 of FIG. 5. In some embodiments, the biochip of FIG. 11 is biochip 604 of FIG. 6. In some embodiments, the biochip of FIG. 11 is biochip 704 of FIG. 7.

At the initialization and calibration phase 1102, a salt buffer solution is flowed through the cells of the nanopore-based sequencing chip at 1112. The salt buffer solution may be potassium choloride (KCl), potassium acetate (KAc), sodium trifluoroacetate (NaTFA), and the like. In some embodiments, performing step 1112 using cartridge 602 of FIG. 6 includes using actuator/motor 618 to rotate radial valve 606 to select port 627, drawing KCl into syringe pump chamber 632 using motor 630, using motor 618 to rotate radial valve 606 to select port 621, and pushing out the KCl in pump chamber 632 to the chamber of biochip 604 via selected port 621. In some embodiments, when a cartridge (e.g., cartridge 502 or FIG. 5 or cartridge 602 of FIG. 6) is utilized in performing the process of FIG. 11, the cartridge is primed for initial use. For example, various materials connected to selectable ports of a selectable valve are primed to draw materials through channels to the selecteable ports for use during the process. Excess materials drawn during priming may be discarded to a waste container (e.g., waste 638 via bypass channel 654 of FIG. 6).

At the membrane formation phase 1104, a membrane, such as a lipid bilayer, is formed over each of the cells. At 1114, a lipid and decane mixture is flowed over the cells. In some embodiments, flowing the lipid and decane mixture includes flowing an air buffer (e.g., air bubble) prior to and after flowing the lipid and decane mixture. Using the example of FIG. 6 to perform step 1114, actuator/motor 618 is used to rotate radial valve 606 to select port 628, air from vent of selectable port 628 is drawn into pump chamber 632 using pump motor 630, motor 618 is used to rotate radial valve 606 to select port 624, a lipid and decane mixture is drawn into chamber 632, motor 618 is used to rotate radial valve 606 to select port 628, air is again drawn into pump chamber 632 using pump motor 630, motor 618 is used to rotate radial valve 606 to select port 621, and then the combination of air buffer, mixture and another air buffer in pump chamber 632 is pushed to the chamber of biochip 604 via selected port 621. As material is flowed over the biochip, the materials that have already flowed across the biochip are pushed into a waste container after exiting the chamber of the biochip.

At 1116, a salt buffer solution is flowed over the cells first, and then an air bubble is flowed over the cells. In an example utilizing a selectable valve, a particular selectable port connected to a salt buffer solution container is selected to draw the salt buffer solution into a pump chamber and another selectable port is selected to draw the air bubble into the pump chamber before pushing the salt buffer and/or air bubble into the chamber of the biochip. One of the purposes of flowing an air bubble over the cells is to facilitate the formation of the lipid bilayer over each of the cells. When an air bubble is flowed over the cells, the thickness of the lipid and decane mixture deposited on the cell is reduced, facilitating the formation of the lipid bilayer.

At 1118, voltage measurements across the lipid bilayers are made to determine whether the lipid bilayers are properly formed. If it is determined that the lipid bilayers are not properly formed, then step 1116 is repeated; otherwise, the process proceeds to step 1120. At 1120, a salt buffer solution is again introduced, and a final air bubble is flowed over the cells. For example, a previously described selectable valve is utilized to draw and push the salt buffer and the air bubble as appropriate from various selectable ports by pushing a combination of an air bubble sandwiched between salt buffer solutions to biochip 604.

At the nanopore formation phase 1106, a nanopore is formed in the bilayer over each of the cells. At 1122, a sample and a pore/polymerase mixture are flowed over the cells. In some embodiments, performing step 1122 using cartridge 602 of FIG. 6 includes using actuator/motor 618 to rotate radial valve 606 to select port 623, drawing a sample and pore/polymerase mixture into pump chamber 632, using motor 618 to rotate radial valve 606 to select port 621, and pushing out the mixture in pump chamber 632 to the chamber of biochip 604 via selected port 621. In order to not disturb the bilayer that has been formed in phase 1104, an air buffer is not introduced between the ending salt buffer solution of 1120 and the sample and pore/polymerase mixture of 1122. In some embodiments, rather than disturbing the nanopore that has been formed by allowing the sample and pore/polymerase mixture to flow completely across the chamber of a biochip and into a waste container, the mixture is pulled from the chamber of the biochip from the chamber opening where the mixture was introduced and the pulled mixture is discarded via a bypass port/channel that does not traverse the chamber of the biochip. For example, using cartridge 602 of FIG. 6, radial valve 606 is configured to select port 621, the sample and pore/polymerase mixture in the chamber of biochip 604 is drawn into pump chamber 632, radial valve 606 is actuated to select port 660 (e.g., in the embodiment of FIG. 6 where bypass channel 654 is directly connected to radial valve 606 via port 660 and valve 650 is replaced with a direct connection between port 621 and the chamber of biochip 604), and the content of pump chamber 632 is discarded to waste container 638 via bypass channel 654 without flowing through chamber port 651.

At sequencing phase 1108, a biological assay (e.g., DNA sequencing) is performed. At 1124, StartMix is flowed over the cells, and the sequencing information is collected and stored. StartMix is a reagent that initiates the sequencing process. In some embodiments, performing step 1124 using cartridge 602 of FIG. 6 includes using actuator/motor 618 to rotate radial valve 606 to select port 622, drawing StartMix into syringe pump chamber 632, using motor 618 to rotate radial valve 606 to select port 621, and pushing out the StartMix in pump chamber 632 to biochip 604 via selected port 621. In order to not disturb the bilayer and nanopore that has been formed, an air buffer is not introduced before the StartMix. After the sequencing phase, one cycle of the process is completed at 1126.

At the cleaning and reset phase 1110, the nanopore-based sequencing biochip is cleaned and reset such that the chip can be recycled for additional uses. For example, a biological assay (e.g., DNA sequencing) of the same sample is performed again. At 1128, a surfactant is flowed over the cells. At 1130, ethanol is flowed over the cells. Although a surfactant and ethanol are used for cleaning the chip in this embodiment, alternative fluids may be used in other embodiments. Steps 1128 and 1130 may also be repeated a plurality of times to ensure that the chip is properly cleaned. In various embodiments, one or more cleaning fluids are obtained via one or more selectable ports of a selectable valve (e.g., radial valve 606 of FIG. 6) to be pushed and flowed over the biochip to be cleaned. After step 1130, the lipid bilayers and pores have been removed and the fluidic workflow process 1100 can be repeated at the initialization and calibration phase 1102 again.

As shown in process 1100 described above, multiple materials with significantly different properties (e.g., compressibility, hydrophobicity, and viscosity) are flowed over an array of sensors on the surface of the nanopore-based sequencing biochip. For improved efficiency, each of the sensors in the array should be exposed to the fluids or gases in a consistent manner. For example, each of the different types of fluids should be flowed over the nanopore-based sequencing chip such that the fluid or gas may be delivered to the chip, evenly coating and contacting all of the cells' surface, and then delivered out of the chip. As described above, a nanopore-based sequencing biochip incorporates a large number of sensor cells configured as an array. As the nanopore-based sequencing chip is scaled to include more and more cells, achieving an even flow of the different types of fluids or gases across the cells of the chip becomes more challenging. Although examples related to FIG. 6 have been discussed in conjunction with the process of FIG. 11, in various embodiments, other selectable ports and cartridges (e.g., using the the components of the examples of FIGS. 5, 7, 8A-8C, 9 etc.) may be utilized to implement the process of FIG. 11.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A delivery system for a sensor chip, comprising:
a plurality of selectable ports arranged on a first assembly, wherein each of the selectable ports is in communication with a separate channel;
the sensor chip, wherein at least one of the separate channels of the selectable ports of the first assembly connects to a flow channel on the sensor chip that allows materials to flow directly on the sensor chip;
a second assembly movable in relation to the first assembly, wherein the second assembly has a central channel that is mechanically connectable to different ones of the plurality of selectable ports on the first assembly by motion of the second assembly relative to the first assembly, the central channel is connected to a pump channel that is separate from the separate channels of the selectable ports of the first assembly, and the pump channel is configured to be selectively disconnected from the flow channel on the sensor chip to draw and hold in the pump channel a material drawn via a first port of the selectable ports of the first assembly when the second assembly is in a first position with respect to the first assembly and the pump channel is configured to deliver the material held in the pump channel to a second port of the first assembly connected to the flow channel on the sensor chip when the second assembly is in a second position with respect to the first assembly that selectively connects the pump channel to the flow channel on the sensor chip; and
a mechanical interface that mechanically engages the second assembly and configured to engage an actuator so that relative motion of the first assembly and the second assembly is affected by the actuator.

2. The system of claim 1, wherein the channel of the second assembly is mechanically connectable at one time to a maximum of only one of the plurality of selectable ports on the first assembly by the motion of the second assembly relative to the first assembly.

3. The system of claim 1, wherein the motion of the second assembly relative to the first assembly automatically seals all other ports of the plurality of selectable ports that have not been selected as a port connected to the channel of the second assembly.

4. The system of claim 1, wherein the sensor chip is a biological assay chip.

5. The system of claim 1, wherein the delivery system is configured to delivery one or more fluids utilized to perform nucleotide sequencing.

6. The system of claim 1, wherein at least one of the plurality of selectable ports is connected to a reagent reservoir.

7. The system of claim 1, wherein at least one of the plurality of selectable ports is connected to a chamber of the sensor chip.

8. The system of claim 1, wherein at least one of the plurality of selectable ports is directly connected to an air vent to enable air to be drawn in the pump channel.

9. The system of claim 1, wherein at least one of the plurality of selectable ports is connected to a source of a gas.

10. The system of claim 1, wherein at least one of the plurality of selectable ports is configured to provide a cleaning solution to be utilized to clean and reset the sensor chip.

11. The system of claim 1, wherein at least one of the plurality of selectable ports is connected to a waste container.

12. The system of claim 11, wherein the waste container is included in a cartridge housing encasing the delivery system.

13. The system of claim 1, wherein the plurality of selectable ports is arranged radially on the first assembly.

14. The system of claim 1, wherein the plurality of selectable ports is arranged linearly on the first assembly.

15. The system of claim 1, wherein the channel of the second assembly is in communication with a two-way pump port.

16. The system of claim 1, wherein the first assembly is configured to be fixed in position while the second assembly moves to select one of the selectable ports.

17. The system of claim 1, wherein the mechanical interface is a part of the second assembly.

18. The system of claim 1, wherein the separate actuator is a motor of an instrument system that is separate from the delivery system.

19. The system of claim 18, wherein the delivery system is included in a replaceable cartridge configured to be engaged with the instrument system.

20. The system of claim 19, wherein the cartridge includes a reagent container, a circuit board, and the sensor chip.

21. The system of claim 1, wherein the second assembly includes a plurality of channels that are fluidically distinct from each another and moveable together with the second assembly.

22. The system of claim 1, wherein the second assembly has a second channel that is mechanically connectable to a second set of one or more ports on a third assembly by motion of the second assembly relative to the third assembly.

23. The system of claim 1, wherein the second assembly has a second channel that is mechanically connectable to a second set of one or more ports on the first assembly by motion of the second assembly relative to the first assembly.

24. The system of claim 1, wherein the second assembly has a second channel that based on its position, selectively connects an outlet chamber port of the sensor chip to a waste container.

25. The system of claim 1, wherein the second assembly includes a pattern detectable by an optical encoder to determine a position of the second assembly.

\* \* \* \* \*